US006825295B2

(12) United States Patent
Klosin et al.

(10) Patent No.: US 6,825,295 B2
(45) Date of Patent: Nov. 30, 2004

(54) ALKARYL-SUBSTITUTED GROUP 4 METAL COMPLEXES, CATALYSTS AND OLEFIN POLYMERIZATION PROCESS

(75) Inventors: Jerzy Klosin, Midland, MI (US); William J. Kruper, Jr., Sanford, MI (US); Peter N. Nickias, Midland, MI (US); Gordon R. Roof, Midland, MI (US); Jorge Soto, Midland, MI (US); David D. Graf, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/154,534

(22) Filed: May 23, 2002

(65) Prior Publication Data

US 2003/0004286 A1 Jan. 2, 2003

Related U.S. Application Data

(63) Continuation-in-part of application No. 09/715,380, filed on Nov. 17, 2000, now Pat. No. 6,515,155.
(60) Provisional application No. 60/170,178, filed on Dec. 10, 1999, provisional application No. 60/170,177, filed on Dec. 10, 1999, and provisional application No. 60/170,175, filed on Dec. 10, 1999.

(51) Int. Cl.[7] .................................................. C08F 4/52
(52) U.S. Cl. ...................... 526/161; 526/172; 526/126; 526/348; 526/352; 526/335
(58) Field of Search .................. 526/172, 161, 526/126; 502/103, 117; 556/51, 52

(56) References Cited

U.S. PATENT DOCUMENTS

| | | | |
|---|---|---|---|
| 5,096,867 A | | 3/1992 | Canich ........................ 502/103 |
| 5,621,126 A | | 4/1997 | Canich et al. ................. 556/9 |
| 5,659,054 A | * | 8/1997 | Wilson ........................... 556/7 |
| 5,965,756 A | * | 10/1999 | McAdon et al. ............... 556/11 |
| 6,015,868 A | | 1/2000 | Nickias et al. ............... 526/127 |
| 6,150,297 A | * | 11/2000 | Campbell et al. ........... 502/152 |
| 6,225,426 B1 | * | 5/2001 | Gillis et al. .................. 526/160 |
| 6,245,868 B1 | * | 6/2001 | Agapiou et al. ............... 526/88 |
| 6,248,912 B1 | * | 6/2001 | Lang et al. ................... 556/11 |
| 6,268,444 B1 | * | 7/2001 | Klosin et al. ................ 526/127 |
| 6,300,433 B1 | * | 10/2001 | Rodriguez et al. .......... 526/127 |
| 6,713,582 B2 | * | 3/2004 | DiMaio et al. .............. 526/281 |
| 2002/0165329 A1 | * | 11/2002 | Klosin et al. ................ 526/126 |
| 2003/0004286 A1 | * | 1/2003 | Klosin et al. ................ 526/126 |

FOREIGN PATENT DOCUMENTS

| | | | |
|---|---|---|---|
| EP | 416815 | 8/1997 | |
| EP | 577581 | 7/2000 | |
| EP | 1 253 158 | 10/2002 | |
| WO | WO 95/07942 | 3/1995 | |
| WO | WO 96/13529 | 5/1996 | |
| WO | WO 98/06727 | 2/1998 | |
| WO | WO 98/06728 A1 * | 2/1998 | ........... C08F/17/00 |
| WO | WO 98/06728 | 2/1998 | |
| WO | WO 00/66596 | * 11/2000 | ........... C07F/7/10 |
| WO | WO 00/69870 | * 11/2000 | ........... C07F/17/00 |
| WO | WO 01/042315 | 6/2001 | |

OTHER PUBLICATIONS

Grant & Hackh's Chemical Dictionary, 5th Ed., McGraw–Hill Book Company, 1987.*
J. Organometallic Chem., E. Barsties et al, vol. 520, pp., 63–68, 1996.
J. Organometallic Chem., H. Plenio et al., vol. 519, pp., 269–272, 1996.

* cited by examiner

Primary Examiner—David W. Wu
Assistant Examiner—Rip A Lee

(57) ABSTRACT

Group 4 metal complexes of the constrained geometry type, catalysts derived therefrom, and polymerization processes using the same, characterized by an alkaryl-substituted silane bridging group are disclosed.

13 Claims, 1 Drawing Sheet

ALKARYL-SUBSTITUTED GROUP 4 METAL COMPLEXES, CATALYSTS AND OLEFIN POLYMERIZATION PROCESS

CROSS-REFERENCE TO RELATED APPLICATIONS

This application is a continuation-in-part of U.S. Ser. No. 09/715,380, filed Nov. 17, 2000, now U.S. Pat. No. 6,515,155, which claims benefit of priority from provisional applications 60/170,178, 60/170,177, and 60/170,175, all filed on Dec. 10, 1999.

FIELD OF THE INVENTION

This invention relates to a class of metal complexes, the ligands used to prepare these metal complexes, polymerization catalysts derived therefrom, and the resulting polymerization processes using the same. More particularly, such metal complexes are characterized by a nitrogen containing aliphatic or cycloaliphatic moiety that is substituted with one or more aryl groups, an aryl-substituted silane bridging group, or one or more Group 14 organometalloid substituents on the metal.

BACKGROUND

EP-A-923,589, which is equivalent to WO98/06727, published Feb. 19, 1998, disclosed Group 4 metal complexes containing a heteroatom substituent at the 3-position of the cyclopentadienyl, especially indenyl, ligand groups. Particular heteroatom containing substituents included dihydrocarbylamino substituents including dimethylamino, diethylamino, methylethylamino, methylphenylamino, dipropylamino, dibutylamino, piperidinyl, morpholinyl, pyrrolidinyl, hexahydro-1H-azepin-1-yl, hexahydro-1(2H)-azocinyl, octahydro-1H-azonin-1-yl, and octahydro-1(2H)-azecinyl.

EP-A-577,581 discloses unsymmetrical bis-Cp metallocenes containing a fluorenyl ligand with heteroatom substituents. E. Barsties; S. Schaible; M.-H. Prosenc; U. Rief; W. Roll; O. Weyland; B. Dorerer; H.-H. Brintzinger *J. Organometallic Chem.* 1996, 520, 63–68, and H. Plenio; D. Birth *J. Organometallic Chem.* 1996, 519, 269–272 disclose systems in which the cyclopentadienyl ring of the indenyl is substituted with a dimethylamino group in non-bridged and Si-bridged bis-indenyl complexes useful for the formation of isotactic polypropylene and polyethylene.

Disclosure of random heteroatom substitution in mono-Cp metallocenes is found in EP-A-416,815, WO 95/07942, WO 96/13529, and U.S. Pat. Nos. 5,096,867 and 5,621,126. Specific heteroatom substitution of the 3- and 2-position of indenyl complexes of group 4 metals was disclosed in WO98/06727 and WO/98/06728 respectively.

Despite the advance in the art, particular higher use temperature, obtained by such prior art metal complexes as were disclosed in the foregoing reference, there remains a desire for improved metal complexes capable of even further increase in use temperature that are still capable of forming catalyst compositions useful in producing polymers having high molecular weights and, for ethylene/higher α-olefin copolymers, high incorporation of comonomer. The subject compositions of this invention show unexpected improvement in these desirable features.

SUMMARY OF THE INVENTION

According to the present invention there are provided metal complexes corresponding to the formula:

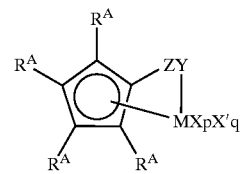

(I)

or

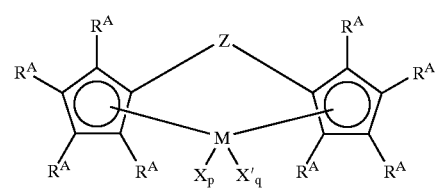

(II)

where M is a Group 4 metal that is in the +2, +3 or +4 formal oxidation state;

$R^A$ independently each occurrence is hydrogen, or a hydrocarbyl, halohydrocarbyl, hydrocarbyloxyhydrocarbyl, dihydrocarbylaminohydrocarbyl, dihydrocarbylamino, hydrocarbyloxy, hydrocarbylsilyl, or trihydrocarbylsilylhydrocarbyl group of from 1 to 80 atoms, not counting hydrogen, or further optionally, two or more $R^A$ groups may be covalently linked together;

Z is $(R^D)_2Si=$, wherein $R^D$ independently each occurrence is $C_{7-20}$ alkaryl or two $R^D$ groups together are alkyl- or polyalkyl-substituted arylene of up to 40 carbons; and Y is bonded to M and Z and is selected from the group consisting of —O—, —S—, —$NR^E$—, and —$PR^E$—; wherein, $R^E$ independently each occurrence is hydrogen, or a member selected from hydrocarbyl, hydrocarbyloxy, silyl, halogenated alkyl, halogenated aryl, and combinations thereof, said $R^E$ having up to 20 nonhydrogen atoms X is an anionic or dianionic ligand group having up to 60 atoms exclusive of the class of ligands that are cyclic, delocalized, π-bound ligand groups;

X' independently each occurrence is a neutral ligand having up to 40 atoms;

p is zero, 1 or 2, and is two less than the formal oxidation state of M when X is an anionic ligand, and when X is a dianionic ligand group, p is 1; and q is zero, 1 or 2.

The above complexes may exist as isolated crystals optionally in pure form or as a mixture with other complexes, in the form of a solvated adduct, optionally in a solvent, especially an organic liquid, in the form of a dimer or chelated derivative thereof, wherein the chelating agent is an organic material, preferably a Lewis base, especially a dihydrocarbylether, cyclic aliphatic ether, trihydrocarbylamine, trihydrocarbylphosphine, or halogenated derivative thereof, or as a polymeric or crosslinked polymeric product, wherein one or more $R^A$ groups are polymerized with one another or copolymerized with an ethylenically unsaturated comonomer.

Also, according to the present invention, there is provided a catalyst composition, useful, inter alia, for the polymerization of addition polymerizable monomers, comprising the following components or the reaction product thereof:

(A) one or more metal complexes of formula (I) or (II); and (B) an activating cocatalyst, wherein the molar ratio of (A) to (B) is from 1:10,000 to 100:1.

Another embodiment of this invention is the foregoing catalyst composition wherein the metal complex is in the form of a radical cation.

Further according to the present invention there is provided a polymerization process comprising contacting one or more addition polymerizable monomers under polymerization conditions with one of the aforementioned catalyst compositions.

A preferred process of this invention is a high temperature solution polymerization process comprising contacting one or more addition polymerizable monomers under polymerization conditions with one of the aforementioned catalyst systems at a temperature from 50° C. to 250° C., preferably from 150° C. to 250° C., most preferably from 175° C. to 220° C. Within the scope of this invention are the polymeric products produced by the aforementioned processes.

This invention also includes the precursor of the delocalized electron containing, cyclic moiety of the metal complex of formula (I), said precursor corresponding to the formula:

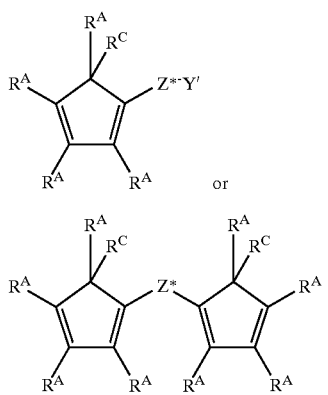

wherein, Y' is —$OR^C$, —$SR^C$, —$NR^C R^E$, —$PR^C R^E$;

$R^C$ independently each occurrence is hydrogen, an alkali metal cation, or a magnesium halide cation, or both $R^C$ groups together are an alkaline earth metal dication;

$Z^*$ is $(R^D)_2 Si=$, wherein $R^D$ independently each occurrence is $C_{7-20}$ alkaryl or two $R^D$ groups together are alkyl- or polyalkyl-substituted arylene of up to 40 carbons; and $R^A$ and $R^E$ are as previously defined.

It is to be understood that the foregoing formulas (IA) and (IIA) depict one of several equivalent interannular, double bond isomers, and that all such isomeric structures are intended to be included by the formulas.

The final embodiment of the invention is the use of one of the foregoing compounds of formula (IA) or (IIA) in a synthesis to produce a Group 4 metal complex of formula (I) or (II).

The present catalysts and processes are especially suited for use in the production of high molecular weight polymers of olefin monomers, over a wide range of polymerization conditions, and especially at elevated temperatures, with exceptionally high catalyst efficiencies. They are especially useful for the solution polymerization of ethylene homopolymers, copolymers of ethylene with an α-olefin other than ethylene (ethylene/α-olefin copolymers), and ethylene/propylene/diene interpolymers (EPDM polymers) wherein the diene is ethylidenenorbornene, 1,4-hexadiene or similar nonconjugated diene. The use of elevated temperatures dramatically increases the productivity of such processes due to the fact that increased polymer solubility at elevated temperatures allows the use of increased conversions (higher concentration of polymer product) without exceeding solution viscosity limitations of the polymerization equipment as well as reduced energy costs needed to devolatilize the reaction product. In the preparation particularly of copolymers of ethylene and at least one α-olefin comonomer, the present catalyst compositions incorporate relatively large quantities of non-ethylene comomomer compared to catalysts comprising a conventional metal. In particular, ethylene/1-octene copolymers having reduced density due to increased incorporation of 1-octene therein, may be made using the present catalyst compositions.

The metal complexes of this invention may also be supported on a support material and used in olefin polymerization processes in a slurry or in the gas phase. Additionally, those complexes wherein $R^A$ is ethylenically unsaturated may be used to form polymeric reaction products via polymerization of copolymerization of such ethylenic unsaturation in the $R^A$ moiety. Such products may be employed in a slurry or gas phase polymerization without need for an additional support material. Such a polymeric catalyst may be formed by prepolymerization of the functionalized metal complex, optionally with one or more ethylenically unsaturated monomers, in situ in a polymerization reactor or in a separate reactor with recovery of the prepolymerized catalyst prior to the primary polymerization process.

DETAILED DESCRIPTION

Figure 1:
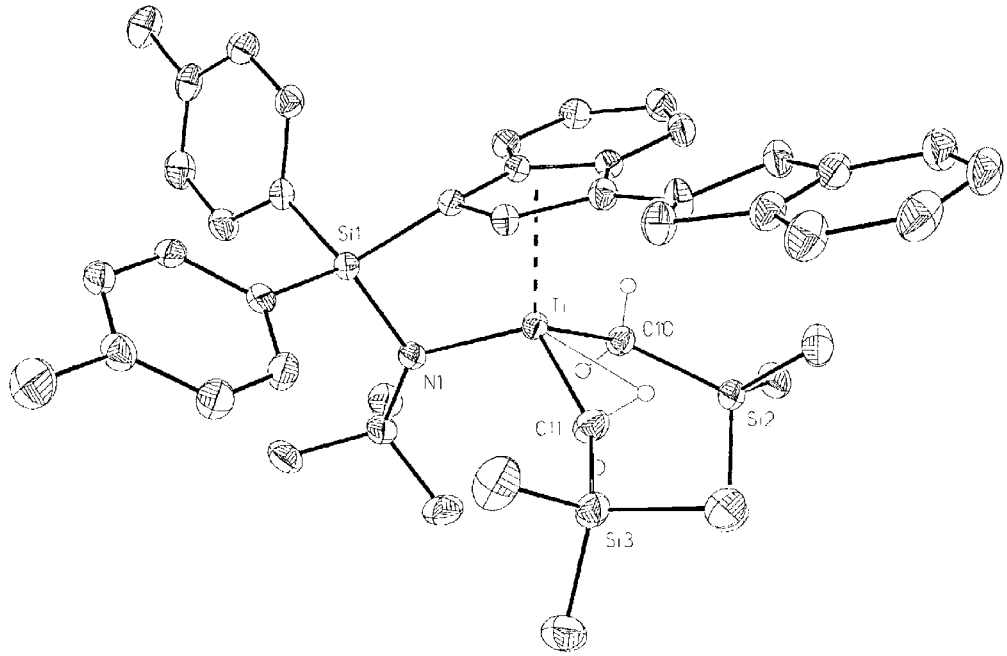
FIG. 1 shows the single crystal structure derived by X-ray analysis (ORTEP) of (N-(1,1-dimethylethyl)-1,1-di(4-methylphenyl)-1-((1,2,3,3a,7a-η)-3-(1,3-dihydro-2H-isoindol-2-yl)-1H-inden-1-yl)silanaminato-(2-)-N-)-[(dimethylsilylene)bis(methylene)] titanium (Example 7).

All reference to the Periodic Table of the Elements herein shall refer to the Periodic Table of the Elements, published and copyrighted by CRC Press, Inc., 1997. Also, any reference to a Group or Groups shall be to the Group or Groups as reflected in this Periodic Table of the Elements using the IUPAC system for numbering groups. As used herein the term "comprising" is not intended to exclude any additional component, additive or step. For purposes of U.S patent practice, the contents of any patent, patent application or publication referenced herein are hereby incorporated by reference in their entirety, especially with respect to the disclosure of synthetic techniques and general knowledge in the art.

In a preferred embodiment of the invention, $R^D$ is $C_{1-10}$ alkyl substituted phenyl group, preferably a $C_{4-10}$ alkyl substituted phenyl group. In addition, it is independently highly desirable that $R^D$ is substituted in the para position or is a mixture of $C_{1-10}$ alkylphenyl substitution isomers. A most preferred $R^D$ group is p-n-butylphenyl.

Preferred compounds according to the invention are those compounds of formula (I) corresponding to the formula:

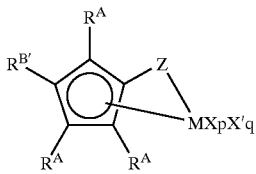

where $R^{B'}$ corresponds to the formula $N(R^B)_2$, wherein $R^B$ each occurrence is $C_{1-10}$ hydrocarbyl, or a halo- or tri($C_{1-4}$ hydrocarbyl)silyl-substituted derivative thereof, or two $R^B$ groups together form a divalent hydrocarbon moiety, or a halo- or tri($C_{1-4}$ hydrocarbyl)silyl-substituted derivative thereof, said divalent group containing from 4 to 40 atoms not counting hydrogen; and $R^A$, Z, M, X, X', p and q are as previously defined.

Most preferably, $N(R^B)_2$, is dibenzylamino or two $R^B$ groups together with the nitrogen atom form a cycloaliphatic group, optionally substituted with an aromatic group. In a most preferred embodiment, the cycloaliphatic group is substituted with an aromatic group, which more preferably still, is a benzannulated ligand, which, together with both $R^B$ groups forms a multiple ring, fused heteroatomic group. Thus, most preferably, —$N(R^B)_2$ is in the form of a multiple ring, fused, aza-cyclic group. Examples of the foregoing, —$N(R^B)_2$ groups include: 1,3-dihydro-2H-isoindol-2-yl, 1,2,3,4-tetrahydro-2H-isoquinoline-2-yl, 1,3-dihydro-2H-benzo[f]isoindol-2-yl, 1,3-dihydro-2H-benzo[e]isoindol-2-yl, 1,2,3,4-tetrahydro-2H-benzo[g]isoquinoline-2-yl, 1,2,3,4-tetrahydro-2H-benzo[f]isoquinoline-2-yl, 1,2,3,4-tetrahydro-2H-benzo[h]isoquinoline-2-yl, 1H-benzo[de]isoquinolin-2(3H)-yl, and dibenzylamino groups, corresponding to the following formulas:

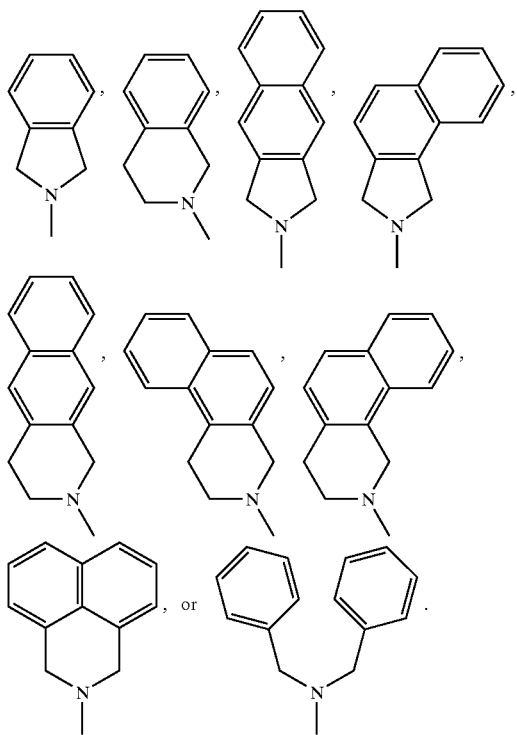

A preferred Group 4 metal for all of the present metal complexes is titanium.

Preferred X groups are halo, $C_{1-10}$ hydrocarbyl or trialkylsilylalkyl groups of up to 20 caarbons, or two such X groups together form a divalent ligand group. Most preferred X groups are chloro, methyl, trimethylsilylmethyl, or two X groups together are (dimethylsilylene)bis-(methylene), most preferably trimethylsilylmethyl, or two X groups together are (dimethylsilylene)bis(methylene). In the embodiments wherein X is trimethylsilylmethyl the complexes possess improved catalytic activity. In the embodiments wherein two X groups together are (dimethylsilylene)bis(methylene) the metal complexes additionally are particularly stable (robust) under typical storage and use conditions.

Preferred $R^A$ groups (other than the —$NR^B$ groups previously disclosed at the 3 position of compounds of formula (I)) are hydrogen, or an alkyl, aryl or aralkyl group of up to 10 carbons.

Preferably in all embodiments of the invention, Y is —$NR^E$— where $R^E$ is $C_{1-6}$ alkyl or cycloalkyl, preferably isopropyl, cyclohexyl, or t-butyl.

Preferred X' groups in all of the foregoing embodiments of the invention are carbon monoxide; phosphines, especially trimethylphosphine, triethylphosphine, triphenylphosphine and bis(1,2-dimethylphosphino)ethane; $P(OR^K)_3$, wherein $R^K$, independently each occurrence, is hydrocarbyl, silyl or silylhydrocarbyl; ethers, especially tetrahydrofuran; amines, especially pyridine, bipyridine, tetramethylethylenediamine (TMEDA), or triethylamine; olefins; and conjugated dienes having from 4 to 40 carbon atoms. Complexes including the latter X' groups, especially terminally hydrocarbyl substituted-1,3-butadienes, include those wherein the metal is in the +2 formal oxidation state.

In the foregoing compounds when p is 2, q is zero, M is in the +3 or +4 formal oxidation state, and X independently each occurrence preferably is chloride, methyl, benzyl, trimethylsilylmethyl, allyl, pyrollyl or two X groups together are 1,4-butane-diyl, 2-butene-1,4-diyl, 2,3-dimethyl-2-butene-1,4-diyl, 2-methyl-2-butene-1,4-diyl, xylyldiyl, or (dimethylsilylene)bis(methylene). Additionally, when p is 1, q is zero, M is in the +3 formal oxidation state, and X is preferably, 2-(N,N-dimethyl) aminobenzyl, 2-(N,N-dimethylaminomethyl)phenyl, allyl, or methallyl. Finally, when p is 0, q is 1, M is in the +2 formal oxidation state, and X' is 1,4-diphenyl-1,3-butadiene, 1,3-pentadiene or 2,4-hexadiene.

Highly preferred complexes according to the invention correspond to the formulas:

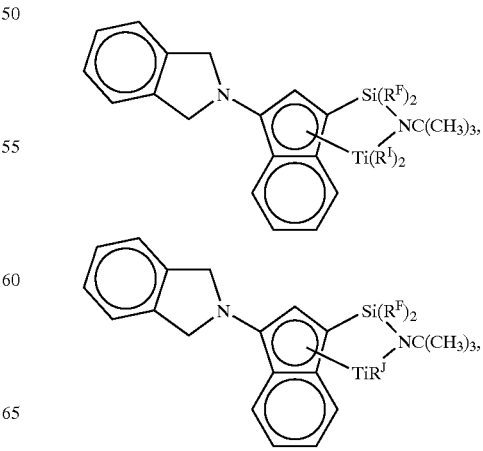

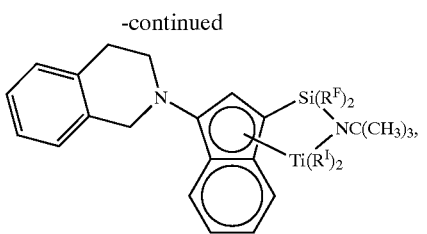
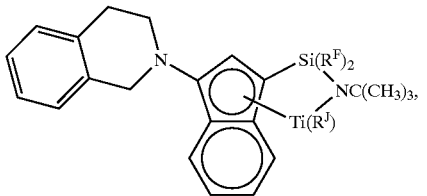
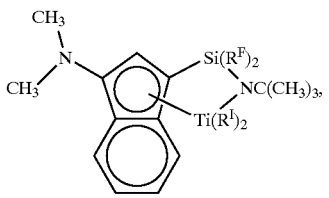
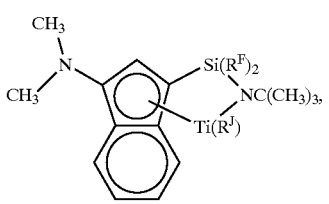
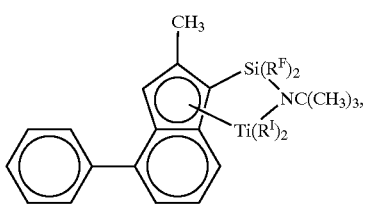
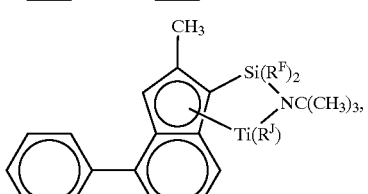
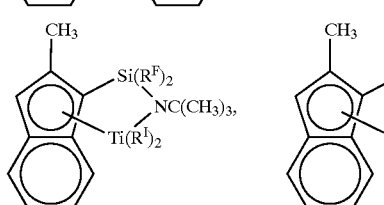
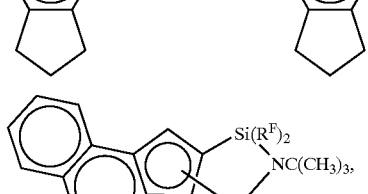
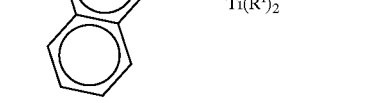

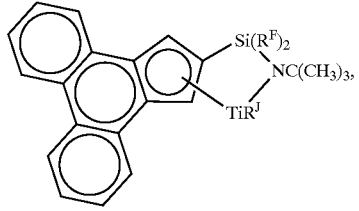
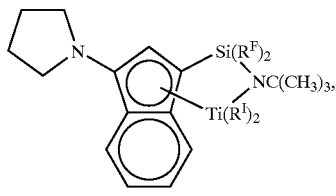
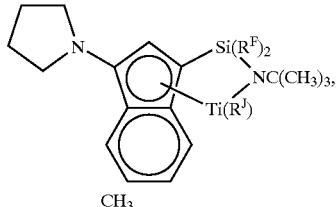
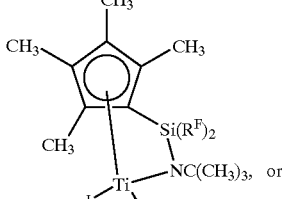
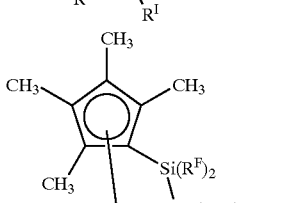

where $R^F$ is $C_{1-10}$ alkyl substituted phenyl, preferably $C_{4-10}$ alkyl substituted phenyl, most preferably n-butylphenyl, most highly preferably para-n-butylphenyl;

$R^I$ is chloro, methyl, benzyl, trimethylsilylmethyl or two $R^I$ groups together are (dimethylsilylene)bis(methylene); and $R^J$ is allyl, 2-(dimethylamino)benzyl, 1,4-pentadiene or 1,4-diphenyl-1,3-butadiene.

Illustrative metal complexes according to the present invention include:

dichloro(N-(1,1-dimethylethyl)-1,1-di(4-n-butyl)phenyl-1-(tetramethyl-η-cyclopentadienyl)silanaminato-(2-)-N-)-titanium;

(N-(1,1-dimethylethyl)-1,1-di(4-n-butyl)phenyl-1-(tetramethyl-η-cyclopentadienyl)silanaminato-(2-)-N-)-titanium dimethyl;

(N-(1,1-dimethylethyl)-1,1-di(4-n-butyl)phenyl-1-(tetramethyl-η-cyclopentadienyl)silanaminato-(2-)-N-)-titanium bis(trimethylsilylmethyl);

(N-(1,1-dimethylethyl)-1,1-di(4-n-butyl)phenyl-1-(tetramethyl-η-cyclopentadienyl)silanaminato-(2-)-N-)-titanium (dimethylsilylene)bis(methylene);

(N-(1,1-dimethylethyl)-1,1-di(4-n-butyl)phenyl-1-(tetramethyl-η-cyclopentadienyl)silanaminato-(2-)-N-)-titanium (III) 2-(N,N-dimethylamino)benzyl;

(N-(1,1-dimethylethyl)-1,1-di(4-n-butyl)phenyl-1-(tetramethyl-η-cyclopentadienyl)silanaminato-(2-)-N-)-titanium (II) 1,4-diphenyl-1,3-butadiene;

dichloro(N-(cyclohexyl)-1,1-di(4-n-butyl)phenyl-1-(tetramethyl-η-cyclopentadienyl)silanaminato-(2-)-N-)-titanium;

(N-(cyclohexyl)-1,1-di(4-n-butyl)phenyl-1-(tetramethyl-η-cyclopentadienyl)silanaminato-(2-)-N-)-titaniumdimethyl;

(N-(cyclohexyl)-1,1-di(4-n-butyl)phenyl-1-(tetramethyl-η-cyclopentadienyl)silanaminato-(2-)-N-)-titanium bis(trimethylsilylmethyl);

(N-(cyclohexyl)-1,1-di(4-n-butyl)phenyl-1-(tetramethyl-η-cyclopentadienyl)silanaminato-(2-)-N-)-titanium (dimethylsilylene)bis(methylene);

(N-(cyclohexyl)-1,1-di(4-n-butyl)phenyl-1-(tetramethyl-η-cyclopentadienyl)silanaminato-(2-)-N-)-titanium (III) 2-(N,N-dimethylamino)benzyl;

(N-(cyclohexyl)-1,1-di(4-n-butyl)phenyl-1-(tetramethyl-η-cyclopentadienyl)silanaminato-(2-)-N-)-titanium (II) 1,4-diphenyl-1,3-butadiene;

dichloro(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium;

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium dimethyl;

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium bis(trimethylsilylmethyl);

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium (dimethylsilylene)bis(methylene);

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium (III) 2-(N,N-dimethylamino)benzyl;

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium (II) 1,4-diphenyl-1,3-butadiene;

dichloro(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium;

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium dimethyl;

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium bis(trimethylsilylmethyl);

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium (dimethylsilylene)bis(methylene);

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium (III) 2-(N,N-dimethylamino)benzyl;

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium (II) 1,4-diphenyl-1,3-butadiene;

dichloro(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium;

(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium dimethyl;

(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium bis(trimethylsilylmethyl);

(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium (dimethylsilylene)bis(methylene);

(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium (III) 2-(N,N-dimethylamino)benzyl;

(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium (II) 1,4-diphenyl-1,3-butadiene;

dichloro(N-(cyclohexyl)-1,1-di(4-methylphenyl)-1-((1,2,3a,7a-η)-2-methyl-4-phenyl-1H-inden-1-yl)silanaminato-(2-)-N-)-titanium;

(N-(cyclohexyl)-1,1-di(4-methylphenyl)-1-((1,2,3,3a,7a-η)-2-methyl-4-phenyl-1H-inden-1-yl)silanaminato-(2-)-N-)-titanium dimethyl;

(N-(cyclohexyl)-1,1-di(4-methylphenyl)-1-((1,2,3,3a,7a-η)-2-methyl-4-phenyl-1H-inden-1-yl)silanaminato-(2-)-N-)-titanium bis(trimethylsilylmethyl);

(N-(cyclohexyl)-1,1-di(4-methylphenyl)-1-((1,2,3,3a,7a-η)-2-methyl-4-phenyl-1H-inden-1-yl)silanaminato-(2-)-N-)-titanium (dimethylsilylene)bis(methylene);

(N-(cyclohexyl)-1,1-di(4-methylphenyl)-1-((1,2,3,3a,7a-η)-2-methyl-4-phenyl-1H-inden-1-yl)silanaminato-(2-)-N-)-titanium (III) 2-(N,N-dimethylamino)benzyl;

(N-(cyclohexyl)-1,1-di(4-methylphenyl)-1-((1,2,3,3a,7a-η)-2-methyl-4-phenyl-1H-inden-1-yl)silanaminato-(2-)-N-)-titanium (II) 1,4-diphenyl-1,3-butadiene;

dichloro(N-(1,1-dimethylethyl)-1,1-di(4-n-butyl)phenyl-1-((1,2,3,3a,7a-η)-3-(1-pyrrolidinyl)-1H-inden-1-yl)silanaminato-(2-)-N-)-titanium;

(N-(1,1-dimethylethyl)-1,1-di(4-n-butyl)phenyl-1-((1,2,3,3a,7a-η)-3-(1-pyrrolidinyl)-1H-inden-1-yl)silanaminato-(2-)-N-)-titanium dimethyl;

(N-(1,1-dimethylethyl)-1,1-di(4-n-butyl)phenyl-1-((1,2,3,3a,7a-η)-3-(1-pyrrolidinyl)-1H-inden-1-yl)silanaminato-(2-)-N-)-titanium bis(trimethylsilylmethyl);

(N-(1,1-dimethylethyl)-1,1-di(4-n-butyl)phenyl-1-((1,2,3,3a,7a-η)-3-(1-pyrrolidinyl)-1H-inden-1-yl)silanaminato-(2-)-N-)-titanium (dimethylsilylene)bis(methylene);

(N-(1,1-dimethylethyl)-1,1-di(4-n-butyl)phenyl-1-((1,2,3,3a,7a-η)-3-(1-pyrrolidinyl)-1H-inden-1-yl)silanaminato-(2-)-N-)-titanium (III) 2-(N,N-dimethylamino)benzyl;

(N-(1,1-dimethylethyl)-1,1-di(4-n-butyl)phenyl-1-((1,2,3,3a,7a-η)-3-(1-pyrrolidinyl)-1H-inden-1-yl)silanaminato-(2-)—N)-titanium (II) 1,4-diphenyl-1,3-butadiene;

dichloro(N-(cyclohexyl)-1,1-di(4-n-butyl)phenyl-1-((1,2,3,3a,7a-η)-3-(1-pyrrolidinyl)-1H-inden-1-yl)silanaminato-(2-)-N-)-titanium;

(N-(cyclohexyl)-1,1-di(4-n-butyl)phenyl-1-((1,2,3,3a,7a-η)-3-(1-pyrrolidinyl)-1H-inden-1-yl)silanaminato-(2-)-N-)-titaniumdimethyl;

(N-(cyclohexyl)-1,1-di(4-n-butyl)phenyl-1-((1,2,3,3a,7a-η)-3-(1-pyrrolidinyl)-1H-inden-1-yl)silanaminato-(2-)-N-)-titanium bis(trimethylsilylmethyl);

(N-(cyclohexyl)-1,1-di(4-n-butyl)phenyl-1-((1,2,3,3a,7a-η)-3-(1-pyrrolidinyl)-1H-inden-1-yl)silanaminato-(2-)-N-)-titanium (dimethylsilylene)bis(methylene);

(N-(cyclohexyl)-1,1-di(4-n-butyl)phenyl-1-((1,2,3,3a,7a-η)-3-(1-pyrrolidinyl)-1H-inden-1-yl)silanaminato-(2-)-N-)-titanium (III) 2-(N,N-dimethylamino)benzyl;

(N-(cyclohexyl)-1,1-di(4-n-butyl)phenyl-1-((1,2,3,3a,7a-η)-3-(1-pyrrolidinyl)-1H-inden-1-yl)silanaminato-(2-)-N-)-titanium (II) 1,4-diphenyl-1,3-butadiene;

dichloro(N-(1,1-dimethylethyl)-1,1-di(4-n-butyl)phenyl-1-((1,2,3,3a,7a-η)-3-(2,3,4,5-tetrahydro-1-pyridinyl)-1H-inden-1-yl)silanaminato-(2-)-N-)-titanium;

(N-(1,1-dimethylethyl)-1,1-di(4-n-butyl)phenyl-1-((1,2,3,3a,7a-η)-3-(2,3,4,5-tetrahydro-1-pyridinyl)-1H-inden-1-yl)silanaminato-(2-)-N-)-titanium dimethyl;

(N-(1,1-dimethylethyl)-1,1-di(4-n-butyl)phenyl-1-((1,2,3,3a,7a-η)-3-(2,3,4,5-tetrahydro-1-pyridinyl)-1H-inden-1-yl)silanaminato-(2-)-N-)-titanium bis(trimethylsilylmethyl);

(N-(1,1-dimethylethyl)-1,1-di(4-n-butyl)phenyl-1-((1,2,3,3a,7a-η)-3-(2,3,4,5-tetrahydro-1-pyridinyl)-1H-inden-1-yl)silanaminato-(2-)-N-)-titanium (dimethylsilylene)bis(methylene);

(N-(1,1-dimethylethyl)-1,1-di(4-n-butyl)phenyl-1-((1,2,3,3a,7a-η)-3-(2,3,4,5-tetrahydro-1-pyridinyl)-1H-inden-1-yl)silanaminato-(2-)-N-)-titanium (III) 2-(N,N-dimethylamino)benzyl;

(N-(1,1-dimethylethyl)-1,1-di(4-n-butyl)phenyl-1-((1,2,3,3a,7a-η)-3-(2,3,4,5-tetrahydro-1-pyridinyl)-1H-inden-1-yl)silanaminato-(2-)-N-)-titanium (II) 1,4-diphenyl-1,3-butadiene;

dichloro(N-(cyclohexyl)-1,1-di(4-n-butyl)phenyl-1-((1,2,3,3a,7a-η)-3-(2,3,4,5-tetrahydro-1-pyridinyl)-1H-inden-1-yl)silanaminato-(2-)-N-)-titanium;

(N-(cyclohexyl)-1,1-di(4-n-butyl)phenyl-1-((1,2,3,3a,7a-η)-3-(2,3,4,5-tetrahydro-1-pyridinyl)-1H-inden-1-yl)silanaminato-(2-)-N-)-titanium dimethyl;

(N-(cyclohexyl)-1,1-di(4-n-butyl)phenyl-1-((1,2,3,3a,7a-η)-3-(2,3,4,5-tetrahydro-1-pyridinyl)-1H-inden-1-yl)silanaminato-(2-)-N-)-titanium bis(trimethylsilylmethyl);

(N-(cyclohexyl)-1,1-di(4-n-butyl)phenyl-1-((1,2,3,3a,7a-η)-3-(2,3,4,5-tetrahydro-1-pyridinyl)-1H-inden-1-yl)silanaminato-(2-)-N-)-titanium (dimethylsilylene)bis(methylene);

(N-(cyclohexyl)-1,1-di(4-n-butyl)phenyl-1-((1,2,3,3a,7a-η)-3-(2,3,4,5-tetrahydro-1-pyridinyl)-1H-inden-1-yl)silanaminato-(2-)-N-)-titanium (III) 2-(N,N-dimethylamino)benzyl;

(N-(cyclohexyl)-1,1-di(4-n-butyl)phenyl-1-((1,2,3,3a,7a-η)-3-(2,3,4,5-tetrahydro-1-pyridinyl)-1H-inden-1-yl)silanaminato-(2-)-N-)-titanium (II) 1,4-diphenyl-1,3-butadiene;

dichloro(N-(1,1-dimethylethyl)-1,1-di(4-n-butyl)phenyl-1-((1,2,3,3a,7a-η)-3-(1,3-dihydro-2H-isoindol-2-yl)-1H-inden-1-yl)silanaminato-(2-)-N-)-titanium;

(N-(1,1-dimethylethyl)-1,1-di(4-n-butyl)phenyl-1-((1,2,3,3a,7a-η)-3-(1,3-dihydro-2H-isoindol-2-yl)-1H-inden-1-yl)silanaminato-(2-)-N-)-titanium dimethyl;

(N-(1,1-dimethylethyl)-1,1-di(4-n-butyl)phenyl-1-((1,2,3,3a,7a-η)-3-(1,3-dihydro-2H-isoindol-2-yl)-1H-inden-1-yl)silanaminato-(2-)-N-)-titanium bis(trimethylsilylmethyl);

(N-(1,1-dimethylethyl)-1,1-di(4-n-butyl)phenyl-1-((1,2,3,3a,7a-η)-3-(1,3-dihydro-2H-isoindol-2-yl)-1H-inden-1-yl)silanaminato-(2-)-N-)-titanium (dimethylsilylene)bis(methylene);

(N-(1,1-dimethylethyl)-1,1-di(4-n-butyl)phenyl-1-((1,2,3,3a,7a-η)-3-(1,3-dihydro-2H-isoindol-2-yl)-1H-inden-1-yl)silanaminato-(2-)-N-)-titanium (III) 2-(N,N-dimethylamino)benzyl;

(N-(1,1-dimethylethyl)-1,1-di(4-n-butyl)phenyl-1-((1,2,3,3a,7a-η)-3-(1,3-dihydro-2H-isoindol-2-yl)-1H-inden-1-yl)silanaminato-(2-)-N-)-titanium (II) 1,4-diphenyl-1,3-butadiene;

dichloro(N-(cyclohexyl)-1,1-di(4-n-butyl)phenyl-1-((1,2,3,3a,7a-η)-3-(1,3-dihydro-2H-isoindol-2-yl)-1H-inden-1-yl)silanaminato-(2-)-N-)-titanium;

(N-(cyclohexyl)-1,1-di(4-n-butyl)phenyl-1-((1,2,3,3a,7a-7)-3-(1,3-dihydro-2H-isoindol-2-yl)-1H-inden-1-yl)silanaminato-(2-)-N-)-titaniumdimethyl;

(N-(cyclohexyl)-1,1-di(4-n-butyl)phenyl-1-((1,2,3,3a,7a-η)-3-(1,3-dihydro-2H-isoindol-2-yl)-1H-inden-1-yl)silanaminato-(2-)-N-)-titanium bis(trimethylsilylmethyl);

(N-(cyclohexyl)-1,1-di(4-n-butyl)phenyl-1-((1,2,3,3a,7a-η)-3-(1,3-dihydro-2H-isoindol-2-yl)-1H-inden-1-yl)silanaminato-(2-)-N-)-titanium (dimethylsilylene)bis(methylene);

(N-(cyclohexyl)-1,1-di(4-n-butyl)phenyl-1-((1,2,3,3a,7a-η)-3-(1,3-dihydro-2H-isoindol-2-yl)-1H-inden-1-yl)silanaminato-(2-)-N-)-titanium (III) 2-(N,N-dimethylamino)benzyl;

(N-(cyclohexyl)-1,1-di(4-n-butyl)phenyl-1-((1,2,3,3a,7a-η)-3-(1,3-dihydro-2H-isoindol-2-yl)-1H-inden-1-yl)silanaminato-(2-)-N-)-titanium (II) 1,4-diphenyl-1,3-butadiene;

dichloro(N-(1,1-dimethylethyl)-1,1-di(4-n-butyl)phenyl-1-((1,2,3,3a,7a-η)-3-(1,2,3,4-tetrahydro-2(1H)-isoquinolinyl)-1H-inden-1-yl)silanaminato-(2-)-N-)-titanium;

(N-(1,1-dimethylethyl)-1,1-di(4-n-butyl)phenyl-1-((1,2,3,3a,7a-η)-3-(1,2,3,4-tetrahydro-2(1H)-isoquinolinyl)-1H-inden-1-yl)silanaminato-(2-)-N-)-titanium dimethyl;

(N-(1,1-dimethylethyl)-1,1-di(4-n-butyl)phenyl-1-((1,2,3,3a,7a-η)-3-(1,2,3,4-tetrahydro-2(1H)-isoquinolinyl)-1H-inden-1-yl)silanaminato-(2-)-N-)-titanium bis(trimethylsilylmethyl);

(N-(1,1-dimethylethyl)-1,1-di(4-n-butyl)phenyl-1-((1,2,3,3a,7a-η)-3-(1,2,3,4-tetrahydro-2(1H)-isoquinolinyl)-1H-inden-1-yl)silanaminato-(2-)-N-)-titanium (dimethylsilylene)bis(methylene);

(N-(1,1-dimethylethyl)-1,1-di(4-n-butyl)phenyl-1-((1,2,3,3a,7a-η)-3-(1,2,3,4-tetrahydro-2(1H)-isoquinolinyl))-1H-inden-1-yl)silanaminato-(2-)-N-)-titanium (III) 2-(N,N-dimethylamino)benzyl;

(N-(1,1-dimethylethyl)-1,1-di(4-n-butyl)phenyl-1-((1,2,3,3a,7a-η)-3-(1,2,3,4-tetrahydro-2(1H)-isoquinolinyl)-1H-inden-1-yl)silanaminato-(2-)-N-)-titanium (II) 1,4-diphenyl-1,3-butadiene;

dichloro(N-(cyclohexyl)-1,1-di(4-n-butyl)phenyl-1-((1,2,3,3a,7a-η)-3-(1,2,3,4-tetrahydro-2(1H)-isoquinolinyl)-1H-inden-1-yl)silanaminato-(2-)-N-)-titanium;

(N-(cyclohexyl)-1,1-di(4-n-butyl)phenyl-1-((1,2,3,3a,7a-η)-3-(1,2,3,4-tetrahydro-2(1H)-isoquinolinyl)-1H-inden-1-yl)silanaminato-(2-)-N-)-titanium dimethyl;

(N-(cyclohexyl)-1,1-di(4-n-butyl)phenyl-1-((1,2,3,3a,7a-η)-3-(1,2,3,4-tetrahydro-2(1H)-isoquinolinyl)-1H-inden-1-yl)silanaminato-(2-)-N-)-titanium bis(trimethylsilylmethyl);

(N-(cyclohexyl)-1,1-di(4-n-butyl)phenyl-1-((1,2,3,3a,7a-η)-3-(1,2,3,4-tetrahydro-2(1H)-isoquinolinyl)-1H-inden-1-yl)silanaminato-(2-)-N-)-titanium (dimethylsilylene)bis(methylene);

(N-(cyclohexyl)-,4-di(4-n-butyl)phenyl-1-((1,2,3,3a,7a-η)-3-(1,2,3,4-tetrahydro-2(1H)-isoquinolinyl)-1H-inden-1-yl)silanaminato-(2-)-N-)-titanium (III) 2-(N,N-dimethylamino)benzyl;

(N-(cyclohexyl)-1,1-di(4-n-butyl)phenyl-1-((1,2,3,3a,7a-η)-3-(1,2,3,4-tetrahydro-2(1H)-isoquinolinyl)-1H-inden-1-yl)silanaminato-(2-)-N-)-titanium (II) 1,4-diphenyl-1,3-butadiene;

dichloro(N-(1,1-dimethylethyl)-1,1-di(4-n-butyl)phenyl-1-((1,2,3,3a,7a-η)-3-(1,3-dihydro-2H-benzo[f]isoindol-2-yl)-1H-inden-1-yl)silanaminato-(2-)-N-)-titanium;

(N-(1,1-dimethylethyl)-1,1-di(4-n-butyl)phenyl-1-((1,2,3,3a,7a-η)-3-(1,3-dihydro-2H-benzo[f]isoindol-2-yl)-1H-inden-1-yl)silanaminato-(2-)-N-)-titanium dimethyl;

(N-(1,1-dimethylethyl)-1,1-di(4-n-butyl)phenyl-1-((1,2,3,3a,7a-η)-3-(1,3-dihydro-2H-benzo[f]isoindol-2-yl)-1H-inden-1-yl)silanaminato-(2-)-N-)-titanium bis(trimethylsilylmethyl);

(N-(1,1-dimethylethyl)-1,1-di(4-n-butyl)phenyl-1-((1,2,3,3a,7a-η)-3-(1,3-dihydro-2H-benzo[f]isoindol-2-yl)-1H-inden-1-yl)silanaminato-(2-)-N-)-titanium (dimethylsilylene)bis(methylene);

(N-(1,1-dimethylethyl)-1,1-di(4-n-butyl)phenyl-1-((1,2,3,3a,7a-η)-3-(1,3-dihydro-2H-benzo[f]isoindol-2-yl)-1H-inden-1-yl)silanaminato-(2-)-N-)-titanium (III) 2-(N,N-dimethylamino)benzyl;

(N-(1,1-dimethylethyl)-1,1-di(4-n-butyl)phenyl-1-((1,2,3,3a,7a-1)-3-(1,3-dihydro-2H-benzo[f]isoindol-2-yl)-1H-inden-1-yl)silanaminato-(2-)-N-)-titanium (II) 1,4-diphenyl-1,3-butadiene;

dichloro(N-(cyclohexyl)-1,1-di(4-n-butyl)phenyl-1-((1,2,3,3a,7a-η)-3-(1,3-dihydro-2H-benzo[f]isoindol-2-yl)-1H-inden-1-yl)silanaminato-(2-)-N-)-titanium;

(N-(cyclohexyl)-1,1-di(4-n-butyl)phenyl-1-((1,2,3,3a,7a-η)-3-(1,3-dihydro-2H-benzo[f]isoindol-2-yl)-1H-inden-1-yl)silanaminato-(2-)-N-)-titanium dimethyl;

(N-(cyclohexyl)-1,1-di(4-n-butyl)phenyl-1-((1,2,3,3a,7a-η)-3-(1,3-dihydro-2H-benzo[f]isoindol-2-yl)-1H-inden-1-yl)silanaminato-(2-)-N-)-titanium bis(trimethylsilylmethyl);

N-(cyclohexyl)-1,1-di(4-n-butyl)phenyl-1-((1,2,3,3a,7a-η)-3-(1,3-dihydro-2H-benzo[f]isoindol-2-yl)-1H-inden-1-yl)silanaminato-(2-)-N-)-titanium (dimethylsilylene)bis(methylene);

(N-(cyclohexyl)-1,1-di(4-n-butyl)phenyl-1-((1,2,3,3a,7a-η)-3-(1,3-dihydro-2H-benzo[f]isoindol-2-yl)-1H-inden-1-yl)silanaminato-(2-)-N-)-titanium (III) 2-(N,N-dimethylamino)benzyl;

(N-(cyclohexyl)-1,1-di(4-n-butyl)phenyl-1-((1,2,3,3a,7a-η)-3-(1,3-dihydro-2H-benzo[f]isoindol-2-yl)-1H-inden-1-yl)silanaminato-(2-)-N-)-titanium (II) 1,4-diphenyl-1,3-butadiene;

dichloro(N-(1,1-dimethylethyl)-1,1-di(4-n-butyl)phenyl-1-((1,2,3,3a,7a-η)-3-(1,3-dihydro-2H-benzo[e]isoindol-2-yl)-1H-inden-1-yl)silanaminato-(2-)-N-)-titanium;

(N-(1,1-dimethylethyl)-1,1-di(4-n-butyl)phenyl-1-((1,2,3,3a,7a-η)-3-(1,3-dihydro-2H-benzo[e]isoindol-2-yl)-1H-inden-1-yl)silanaminato-(2-)-N-)-titanium dimethyl;

(N-(1,1-dimethylethyl)-1,1-di(4-n-butyl)phenyl-1-((1,2,3,3a,7a-η)-3-(1,3-dihydro-2H-benzo[e]isoindol-2-yl)-1H-inden-1-yl)silanaminato-(2-)-N-)-titanium bis(trimethylsilylmethyl);

(N-(1,1-dimethylethyl)-1,1-di(4-n-butyl)phenyl-1-((1,2,3,3a,7a-η)-3-(1,3-dihydro-2H-benzo[e]isoindol-2-yl)-1H-inden-1-yl)silanaminato-(2-)-N-)-titanium (dimethylsilylene)bis(methylene);

(N-(1,1-dimethylethyl)-1,1-di(4-n-butyl)phenyl-1-((1,2,3,3a,7a-η)-3-(1,3-dihydro-2H-benzo[e]isoindol-2-yl)-1H-inden-1-yl)silanaminato-(2-)-N-)-titanium (III) 2-(N,N-dimethylamino)benzyl;

(N-(1,1-dimethylethyl)-1,1-di(4-n-butyl)phenyl-1-((1,2,3,3a,7a-η)-3-(1,3-dihydro-2H-benzo[e]isoindol-2-yl)-1H-inden-1-yl)silanaminato-(2-)-N-)-titanium (II) 1,4-diphenyl-1,3-butadiene;

dichloro(N-(cyclohexyl)-1,1-di(4-n-butyl)phenyl-1-((1,2,3,3a,7a-η)-3-(1,3-dihydro-2H-benzo[e]isoindol-2-yl)-1H-inden-1-yl)silanaminato-(2-)-N-)-titanium;

(N-(cyclohexyl)-1,1-di(4-n-butyl)phenyl-1-((1,2,3,3a,7a-η)-3-(1,3-dihydro-2H-benzo[e]isoindol-2-yl)-1H-inden-1-yl)silanaminato-(2-)-N-)-titanium dimethyl;

(N-(cyclohexyl)-1,1-di(4-n-butyl)phenyl-1-((1,2,3,3a,7a-η)-3-(1,3-dihydro-2H-benzo[e]isoindol-2-yl)-1H-inden-1-yl)silanaminato-(2-)-N-)-titanium bis(trimethylsilylmethyl);

(N-(cyclohexyl)-1,1-di(4-n-butyl)phenyl-1-((1,2,3,3a,7a-η)-3-(1,3-dihydro-2H-benzo[e]isoindol-2-yl)-1H-inden-1-yl)silanaminato-(2-)-N-)-titanium (dimethylsilylene)bis(methylene);

(N-(cyclohexyl)-1,1-di(4-n-butyl)phenyl-1-((1,2,3,3a,7a-η)-3-(1,3-dihydro-2H-benzo[e]isoindol-2-yl)-1H-inden-1-yl)silanaminato-(2-)-N-)-titanium (III) 2-(N,N-dimethylamino)benzyl;

(N-(cyclohexyl)-1,1-di(4-n-butyl)phenyl-1-((1,2,3,3a,7a-η)-3-(1,3-dihydro-2H-benzo[e]isoindol-2-yl)-1H-inden-1-yl)silanaminato-(2-)-N-)-titanium (II) 1,4-diphenyl-1,3-butadiene;

dichloro(N-(1,1-dimethylethyl)-1,1-di(4-n-butyl)phenyl-1-((1,2,3,3a,7a-η)-3-(N,N-dibenzylamino)-1H-inden-1-yl)silanaminato-(2-)-N-)-titanium;

(N-(1,1-dimethylethyl)-1,1-di(4-n-butyl)phenyl-1-((1,2,3,3a,7a-η)-3-(N,N-dibenzylamino)-1H-inden-1-yl)silanaminato-(2-)-N-)-titanium dimethyl;

(N-(1,1-dimethylethyl)-,4-di(4-n-butyl)phenyl-1-((1,2,3,3a,7a-η)-3-(N,N-dibenzylamino)-1H-inden-1-yl)silanaminato-(2-)-N-)-titanium bis(trimethylsilylmethyl);

(N-(1,1-dimethylethyl)-1,1-di(4-n-butyl)iphenyl-1-((1,2,3,3a,7a-η)-3-(N,N-dibenzylamino)-1H-inden-1-yl)silanaminato-(2-)-N-)-titanium (dimethylsilylene)bis(methylene);

(N-(1,1-dimethylethyl)-1,1-di(4-n-butyl)phenyl-1-((1,2,3,3a,7a-η)-3-(N,N-dibenzylamino)-1H-inden-1-yl)silanaminato-(2-)-N-)-titanium (III) 2-(N,N-dimethylamino)benzyl;

(N-(1,1-dimethylethyl)-1,1-di(4-n-butyl)phenyl-1-((1,2,3,3a,7a-η)-3-(N,N-dibenzylamino)-1H-indene-1-yl)silanaminato-(2-)-N-)-titanium (II) 1,4-diphenyl-1,3-butadiene;

dichloro(N-(cyclohexyl)-1,1-di(4-n-butyl)phenyl-1-((1,2,3,3a,7a-η)-3-(N,N-dibenzylamino)-1H-inden-1-yl)silanaminato-(2-)-N-)-titanium;

(N-(cyclohexyl)-1,1-di(4-n-butyl)phenyl-1-((1,2,3,3a,7a-η)-3-(N,N-dibenzylamino)-1H-inden-1-yl)silanaminato-(2-)-N-)-titanium dimethyl;

(N-(cyclohexyl)-1,1-di(4-n-butyl)phenyl-1-((1,2,3,3a,7a-η)-3-(N,N-dibenzylamino)-1H-inden-1-yl)silanaminato-(2-)-N-)-titanium bis(trimethylsilylmethyl);

N-(cyclohexyl)-1,1-di(4-n-butyl)phenyl-1-((1,2,3,3a,7a-η)-3-(N,N-dibenzylamino)-1H-inden-1-yl)silanaminato-(2-)-N-)-titanium (dimethylsilylene)bis(methylene);

(N-(cyclohexyl)-1,1-di(4-n-butyl)phenyl-1-((1,2,3,3a,7a-η)-3-(N,N-dibenzylamino)-1H-inden-1-yl)silanaminato-(2-)-N-)-titanium (III) 2-(N,N-dimethylamino)benzyl; and (N-(cyclohexyl)-1,1-di(4-n-butyl)phenyl-1-((1,2,3,3a,7a-η)-3-(N,N-dibenzylamino)-1H-inden-1-yl)silanaminato-(2-)-N-)-titanium (II) 1,4-diphenyl-1,3-butadiene.

The complexes can be prepared by use of well known synthetic techniques. The reactions are conducted in a suitable noninterfering solvent at a temperature from −100 to 300° C., preferably from −78 to 100° C., most preferably from 0 to 50° C. Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof, cyclic and alicyclic hydrocarbons such as cyclohexane, cycloheptane, methylcyclohexane, methylcycloheptane, and mixtures thereof, aromatic and hydrocarbyl-substituted aromatic compounds such as benzene, toluene, and xylene, $C_{1-4}$ dialkyl ethers, $C_{1-4}$ dialkyl ether derivatives of (poly) alkylene glycols, and tetrahydrofuran. Mixtures of the foregoing are also suitable.

Optionally a reducing agent can be employed to produce the lower oxidation state complexes. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal. Suitable techniques for preparing complexes of the present invention are well known to the skilled artisan and may be readily derived from techniques taught, for example, in the previously mentioned publication, WO98/06727 (U.S. Ser. No. 230,185, filed Jul. 28, 1997).

The complexes are rendered catalytically active by combination with an activating cocatalyst or use of an activating technique, such as those that are previously known in the art for use with Group 4 metal olefin polymerization complexes. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl) borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. 5,153,157, U.S. Pat. No. 5,064,802, U.S. Pat. No. 5,321,106, U.S. Pat. No. 5,721,185, U.S. Pat. No. 5,350,723, U.S. Pat. No. 5,425,872, U.S. Pat. No. 5,625,087, U.S. Pat. No. 5,883,204, U.S. Pat. No. 5,919,983, U.S. Pat. No. 5,783,512, WO 99/15534, and U.S. Ser. No. 09/251,664, filed Feb. 17, 1999.

Combinations of neutral Lewis acids, especially the combination of a trialkylaluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluoro-phenylborane:alumoxane are from 1:1:1 to 1:10:30, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gallium, niobium or tantalum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

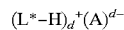

wherein:

L* is a neutral Lewis base;

$(L^*-H)^+$ is a conjugate Bronsted acid of L*;

$A^{d-}$ is a noncoordinating, compatible anion having a charge of d−, and d is an integer from 1 to 3.

More preferably $A^{d-}$ corresponds to the formula: $[M'Q_4]^-$; wherein:

M' is boron or aluminum in the +3 formal oxidation state; and

Q independently each occurrence is selected from hydride, dialkylamido, halide, hydrocarbyl, hydrocarbyloxide, halo-substituted hydrocarbyl, halo-substituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is A⁻. Activating cocatalysts comprising boron which are particularly useful in the preparation of catalysts of this invention may be represented by the following general formula:

$$(L^*-H)^+(BQ_4)^-;$$

wherein:

L* is as previously defined;

B is boron in a formal oxidation state of 3; and

Q is a hydrocarbyl-, hydrocarbyloxy-, fluorohydrocarbyl-, fluorohydrocarbyloxy-, hydroxyfluorohydrocarbyl-, dihydrocarbylaluminumoxyfluorohydrocarbyl-, or fluorinated silylhydrocarbyl-group of up to 20 nonhydrogen atoms, with the proviso that in not more than one occasion is Q hydrocarbyl. Most preferably, Q is each occurrence a fluorinated aryl group, especially, a pentafluorophenyl group.

Preferred Lewis base salts are ammonium salts, more preferably trialkylammonium salts containing one or more $C_{12-40}$ alkyl groups.

Illustrative, but not limiting, examples of boron compounds which may be used as an activating cocatalyst in the preparation of the improved catalysts of this invention are tri-substituted ammonium salts such as:

trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-dimethylanilinium n-butyltris(pentafluorophenyl)borate,
N,N-dimethylanilinium benzyltris(pentafluorophenyl)borate,
N,N-dimethylanilinium tetrakis(4-(t-butyldimethylsilyl)-2,3,5,6-tetrafluorophenyl)borate,
N,N-dimethylanilinium tetrakis(4-(triisopropylsilyl)-2,3,5,6-tetrafluorophenyl)borate,
N,N-dimethylanilinium pentafluorophenoxytris(pentafluorophenyl)borate,
N,N-diethylanilinium tetrakis(pentafluorophenyl)borate,
N,N-dimethyl-2,4,6-trimethylanilinium tetrakis(pentafluorophenyl)borate,
dimethyltetradecylammonium tetrakis(pentafluorophenyl)borate,
dimethylhexadecylammonium tetrakis(pentafluorophenyl)borate,
dimethyloctadecylammonium tetrakis(pentafluorophenyl)borate,
methylditetradecylammonium tetrakis(pentafluorophenyl)borate,
methylditetradecylammonium(hydroxyphenyl)tris(pentafluorophenyl)borate,
methylditetradecylammonium(diethylaluminoxyphenyl)tris(pentafluorophenyl)borate,
methyldihexadecylammonium tetrakis(pentafluorophenyl)borate,
methyldihexadecylammonium(hydroxyphenyl)tris(pentafluorophenyl)borate,
methyldihexadecylammonium(diethylaluminoxyphenyl)tris(pentafluorophenyl)borate,
methyldioctadecylammonium tetrakis(pentafluorophenyl)borate,
methyldioctadecylammonium(hydroxyphenyl)tris(pentafluorophenyl)borate,
methyldioctadecylammonium(diethylaluminoxyphenyl)tris(pentafluorophenyl)borate,
mixtures of the foregoing,
dialkyl ammonium salts such as:
di-(i-propyl)ammonium tetrakis(pentafluorophenyl)borate,
methyloctadecylammonium tetrakis(pentafluorophenyl)borate,
methyloctadodecylammonium tetrakis(pentafluorophenyl)borate, and
dioctadecylammonium tetrakis(pentafluorophenyl)borate;
tri-substituted phosphonium salts such as:
triphenylphosphonium tetrakis(pentafluorophenyl)borate,
methyldioctadecylphosphonium tetrakis(pentafluorophenyl)borate, and tri(2,6-dimethylphenyl)phosphonium tetrakis(pentafluorophenyl)borate;
di-substituted oxonium salts such as:
diphenyloxonium tetrakis(pentafluorophenyl)borate,
di(o-tolyl)oxonium tetrakis(pentafluorophenyl)borate, and
di(octadecyl)oxonium tetrakis(pentafluorophenyl)borate;
di-substituted sulfonium salts such as:
di(o-tolyl)sulfonium tetrakis(pentafluorophenyl)borate, and
methylcotadecylsulfonium tetrakis(pentafluorophenyl)borate.

Preferred $(L^*-H)^+$ cations are methyldioctadecylammonium and dimethyloctadecylammonium. The use of the above Bronsted acid salts as activating cocatalysts for addition polymerization catalysts is known in the art, having been disclosed in U.S. Pat. Nos. 5,064,802, 5,919,983, 5,783,512 and elsewhere.

Another suitable ion forming, activating cocatalyst comprises a salt of a cationic oxidizing agent and a noncoordinating, compatible anion represented by the formula:

$$(Ox^{e+})_d(A^{d-})_e.$$

wherein:

$Ox^{e+}$ is a cationic oxidizing agent having a charge of e+;

e is an integer from 1 to 3; and $A^{d-}$ and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis(pentafluorophenyl)borate. The use of the above salts as activating cocatalysts for addition polymerization catalysts is known in the art, having been disclosed in U.S. Pat. No. 5,321,106.

Another suitable ion forming, activating cocatalyst comprises a compound which is a salt of a carbenium ion and a noncoordinating, compatible anion represented by the formula:

$$©^+A^-$$

wherein:

©⁺ is a $C_{1-20}$ carbenium ion; and

A⁻ is as previously defined. A preferred carbenium ion is the trityl cation, that is triphenylmethylium. The use of the above carbenium salts as activating cocatalysts for addition polymerization catalysts is known in the art, having been disclosed in U.S. Pat. No. 5,350,723.

A further suitable ion forming, activating cocatalyst comprises a compound which is a salt of a silylium ion and a noncoordinating, compatible anion represented by the formula:

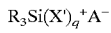

wherein:

R is $C_{1-10}$ hydrocarbyl, and X', q and A⁻ are as previously defined.

Preferred silylium salt activating cocatalysts are trimethylsilylium tetrakispentafluorophenylborate, triethylsilylium tetrakispentafluorophenylborate and ether substituted adducts thereof. The use of the above silylium salts as activating cocatalysts for addition polymerization catalysts is known in the art, having been disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

Another class of suitable catalyst activators are expanded anionic compounds corresponding to the formula:

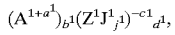

wherein:

$A^1$ is a cation of charge $+a^1$, $Z^1$ is an anion group of from 1 to 50, preferably 1 to 30 atoms, not counting hydrogen atoms, further containing two or more Lewis base sites;

$J^1$ independently each occurrence is a Lewis acid coordinated to at least one Lewis base site of $Z^1$, and optionally two or more such $J^1$ groups may be joined together in a moiety having multiple Lewis acidic functionality, $j^1$ is a number from 2 to 12 and $a^1, b^1, c^1$, and $d^1$ are integers from 1 to 3, with the proviso that $a^1 \times b^1$ is equal to $c^1 \times d^1$.

The foregoing cocatalysts (illustrated by those having imidazolide, substituted imidazolide, imidazolinide, substituted imidazolinide, benzimidazolide, or substituted benzimidazolide anions) may be depicted schematically as follows:

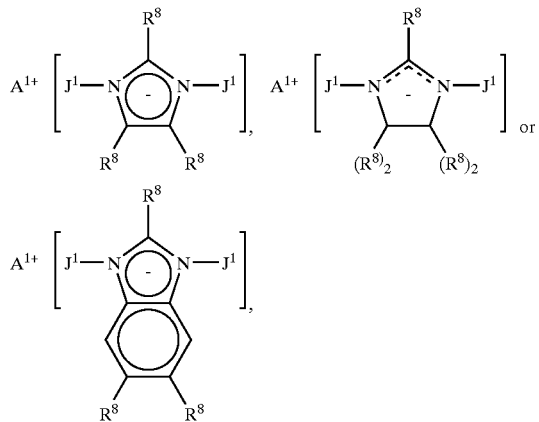

wherein:

$A^{1+}$ is a monovalent cation as previously defined, and preferably is a trihydrocarbyl ammonium cation, containing one or two $C_{10-40}$ alkyl groups, especially the methylbis (tetradecyl)ammonium- or methylbis(octadecyl) ammonium-cation, $R^8$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^1$ is tris(pentafluorophenyl)borane or tris (pentafluorophenyl)aluminane.

Examples of these catalyst activators include the trihydrocarbylammonium-, especially, methylbis(tetradecyl) ammonium- or methylbis(octadecyl)ammonium-salts of:

bis(tris(pentafluorophenyl)borane)imidazolide,
bis(tris(pentafluorophenyl)borane)-2-undecylimidazolide,
bis(tris(pentafluorophenyl)borane)-2-heptadecylimidazolide, bis(tris(pentafluorophenyl) borane)-4,5-bis(undecyl)imidazolide,
bis(tris(pentafluorophenyl)borane)-4,5-bis(heptadecyl) imidazolide,
bis(tris(pentafluorophenyl)borane)imidazolinide,
bis(tris(pentafluorophenyl)borane)-2-undecylimidazolinide,
bis(tris(pentafluorophenyl)borane)-2-heptadecylimidazolinide, bis(tris(pentafluorophenyl) borane)-4,5-bis(undecyl)imidazolinide,
bis(tris(pentafluorophenyl)borane)-4,5-bis(heptadecyl) imidazolinide,
bis(tris(pentafluorophenyl)borane)-5,6-dimethylbenzimidazolide,
bis(tris(pentafluorophenyl)borane)-5,6-bis(undecyl) benzimidazolide,
bis(tris(pentafluorophenyl)alumane)imidazolide,
bis(tris(pentafluorophenyl)alumane)-2-undecylimidazolide,
bis(tris(pentafluorophenyl)alumane)-2-heptadecylimidazolide, bis(tris(pentafluorophenyl) alumane)-4,5-bis(undecyl)imidazolide,
bis(tris(pentafluorophenyl)alumane)-4,5-bis(heptadecyl) imidazolide,
bis(tris(pentafluorophenyl)alumane)imidazolinide,
bis(tris(pentafluorophenyl)alumane)-2-undecylimidazolinide, bis(tris(pentafluorophenyl) alumane)-2-heptadecylimidazolinide, bis(tris (pentafluorophenyl)alumane)-4,5-bis(undecyl) imidazolinide,
bis(tris(pentafluorophenyl)alumane)-4,5-bis(heptadecyl) imidazolinide,
bis(tris(pentafluorophenyl)alumane)-5,6-dimethylbenzimidazolide, and
bis(tris(pentafluorophenyl)alumane)-5,6-bis(undecyl) benzimidazolide.

A further class of suitable activating cocatalysts include cationic Group 13 salts corresponding to the formula:

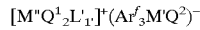

wherein:

M" is aluminum, gallium, or indium;

M' is boron or aluminum;

$Q^1$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^1$ groups may be covalently linked with each other to form one or more fused rings or ring systems;

$Q^2$ is an alkyl group, optionally substituted with one or more cycloalkyl or aryl groups, said $Q^2$ having from 1 to 30 carbons;

L' is a monodentate or polydentate Lewis base, preferably L' is reversibly coordinated to the metal complex such that it may be displaced by an olefin monomer, more preferably L' is a monodentate Lewis base;

l' is a number greater than zero indicating the number of Lewis base moieties, L', and $Ar^f$ independently each occurrence is an anionic ligand group; preferably $Ar^f$ is selected from the group consisting of halide, $C_{1-20}$ halohydrocarbyl, and $Q^1$ ligand groups, more preferably $Ar^f$ is a fluorinated hydrocarbyl moiety of from 1 to 30 carbon atoms, most preferably $Ar^f$ is a fluorinated aromatic hydrocarbyl moiety of from 6 to 30 carbon atoms, and most highly preferably $Ar^f$ is a perfluorinated aromatic hydrocarbyl moiety of from 6 to 30 carbon atoms.

Examples of the foregoing Group 13 metal salts are alumicinium tris(fluoroaryl)borates or gallicinium tris (fluoroaryl)borates corresponding to the formula: $[M''Q^1{}_2L'{}_{l'}]^+(Ar^f{}_3BQ^2)^-$, wherein M'' is aluminum or gallium; $Q^1$ is $C_{1-20}$ hydrocarbyl, preferably $C_{1-8}$ alkyl; $Ar^f$ is perfluoroaryl, preferably pentafluorophenyl; and $Q^2$ is $C_{1-8}$ alkyl, preferably $C_{1-8}$ alkyl. More preferably, $Q^1$ and $Q^2$ are identical $C_{1-8}$ alkyl groups, most preferably, methyl, ethyl or octyl.

The foregoing activating cocatalysts may also be used in combination. An especially preferred combination is a mixture of a tri(hydrocarbyl)aluminum or tri(hydrocarbyl) borane compound having from 1 to 4 carbons in each hydrocarbyl group or an ammonium borate with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris (pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The catalysts, whether or not supported in any suitable manner, may be used to polymerize ethylenically unsaturated monomers having from 2 to 100,000 carbon atoms either alone or in combination. Preferred addition polymerizable monomers for use herein include olefins, diolefins and mixtures thereof. Preferred olefins are aliphatic or aromatic compounds containing vinylic unsaturation as well as cyclic compounds containing ethylenic unsaturation. Examples of the latter include cyclobutene, cyclopentene, norbornene, and norbornene derivatives that are substituted in the 5- and 6-positions with $C_{1-20}$ hydrocarbyl groups. Preferred diolefins are $C_{4-40}$ diolefin compounds, including ethylidene norbornene, 1,4-hexadiene, norbornadiene, and the like. The catalysts and processes herein are especially suited for use in preparation of ethylene/1-butene, ethylene/1-hexene, ethylene/styrene, ethylene/propylene, ethylene/1-pentene, ethylene/4-methyl-1-pentene and ethylene/1-octene copolymers as well as terpolymers of ethylene, propylene and a nonconjugated diene, such as, for example, EPDM terpolymers.

Most preferred monomers include the $C_{2-20}$ α-olefins, especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

Preferred monomers include a combination of ethylene and one or more comonomers selected from monovinyl aromatic monomers, 4-vinylcyclohexene, vinylcyclohexane, norbornadiene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{4-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a nonconjugated diene, especially ethylidenenorbornene or 1,4-hexadiene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from $1:10^6$ to $1:10^3$, more preferably from $1:10^6$ to $1:10^4$.

In most polymerization reactions the molar ratio of catalyst:polymerizable compounds employed is from $10^{-12}:1$ to $10^{-1}:1$, more preferably from $10^{-9}:1$ to $10^{-5}:1$.

Suitable solvents use for solution polymerization are liquids that are substantially inert under process conditions encountered in their usage. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in the same reactor or in separate reactors connected in series or in parallel to prepare polymer blends having desirable properties. An example of such a process is disclosed in WO 94/00500.

The catalysts of the present invention are particularly advantageous for the production of ethylene homopolymers and ethylene/α-olefin copolymers having high levels of long chain branching. The use of the catalysts of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalyst compositions advantageously allows for the economical production of ethylene/α-olefin copolymers having processability similar to high pressure, free radical produced low density polyethylene.

The present catalyst compositions may be advantageously employed to prepare olefin polymers having improved processing properties by polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise ethylene, a $C_{3-20}$ α-olefin and a "H"-branching comonomer. Preferably, such polymers are produced in a solution process, most preferably a continuous solution process.

The catalyst composition may be prepared as a homogeneous catalyst by addition of the requisite components to a solvent or diluent in which polymerization will be conducted. The catalyst composition may also be prepared and employed as a heterogeneous catalyst by adsorbing, depositing or chemically attaching the requisite components on an inorganic or organic particulated solid. Examples of such solids include, silica, silica gel, alumina, clays, expanded clays (aerogels), aluminosilicates, trialkylaluminum compounds, and organic or inorganic polymeric materials, especially polyolefins. In a preferred embodiment, a heterogeneous catalyst is prepared by reacting an inorganic compound, preferably a tri($C_{1-4}$ alkyl)aluminum compound, with an activating cocatalyst, especially an ammonium salt of a hydroxyaryl(trispentafluorophenyl)borate, such as an ammonium salt of (4-hydroxy-3,5-ditertiarybutylphenyl) tris-(pentafluorophenyl)borate or (4-hydroxyphenyl)-tris (pentafluorophenyl)borate. This activating cocatalyst is deposited onto the support by coprecipitating, imbibing, spraying, or similar technique, and thereafter removing any solvent or diluent. The metal complex is added to the support, also by adsorbing, depositing or chemically attaching the same to the support, either subsequently, simultaneously or prior to addition of the activating cocatalyst.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise, the α-olefin monomer or a mixture of different α-olefin monomers may be used in whole or part as the diluent. Most preferably, at least a major part of the diluent comprises the α-olefin monomer or monomers to be polymerized. A dispersant, particularly an elastomer, may be dissolved in the diluent utilizing techniques known in the art, if desired.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas, such as, for example, nitrogen.

The polymerization may be carried out as a batchwise or a continuous polymerization process. A continuous process is preferred, in which event catalyst, ethylene, comonomer, and optionally solvent, are continuously supplied to the reaction zone, and polymer product continuously removed therefrom.

Without limiting in any way the scope of the invention, one means for carrying out such a polymerization process is as follows: In a stirred-tank reactor, the monomers to be polymerized are introduced continuously, together with solvent and an optional chain transfer agent. The reactor contains a liquid phase composed substantially of monomers, together with any solvent or additional diluent and dissolved polymer. If desired, a small amount of a "H"-branch inducing diene such as norbornadiene, 1,7-octadiene or 1,9-decadiene may also be added. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mention chain transfer agent, such as a stream of hydrogen introduced to the reactor, as is well known in the art. The reactor effluent is contacted with a catalyst kill agent such as water. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from about 5 minutes to 8 hours, and preferably from 10 minutes to 6 hours.

Ethylene homopolymers and ethylene/α-olefin copolymers are particularly suited for preparation according to the invention. Generally such polymers have densities from 0.85 to 0.96 g/ml. Typically the molar ratio of α-olefin comonomer to ethylene used in the polymerization may be varied in order to adjust the density of the resulting polymer. When producing materials with a density range of from 0.91 to 0.93 the comonomer to monomer ratio is less than 0.2, preferably less than 0.05, even more preferably less than 0.02, and may even be less than 0.01. In the above polymerization process hydrogen has been found to effectively control the molecular weight of the resulting polymer. Typically, the molar ratio of hydrogen to monomer is less than about 0.5, preferably less than 0.2, more preferably less than 0.05, even more preferably less than 0.02 and may even be less than 0.01.

The polymerization of ethylene in combination with a diene, especially conjugated dienes and polycyclic bulky dienes such as ethylidene norbornene, optionally in the presence of a third monomer, especially a $C_{3-12}$ α-olefin, is particularly advantageously accomplished by the use of metal complexes according to the present invention according to formula (I) containing a 2-alkyl-4-arylinden-1-yl substituent of up to 30 total carbon atoms, especially a 2-methyl-4-phenylinden-1-yl or 2-methyl-4-naphthylinden- 1-yl group. That is, preferred metal complexes are those of formula (I) wherein:

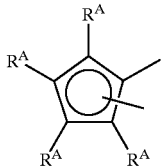

is a 2-alkyl-4-arylinden-1-yl group of up to 30 total carbon atoms.

Surprisingly, the activity of catalysts comprising the foregoing metal complexes is relatively unaffected by the diene in comparison with similar metal complexes lacking in the foregoing structure, and the resulting polymers contain relative large quantities of the polymerized diene. Especially preferred metal complexes for the foregoing polymerization are:

dichloro(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium;

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium dimethyl;

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium bis(trimethylsilylmethyl);

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium (dimethylsilylene)bis(methylene);

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium (III) 2-(N,N-dimethylamino)benzyl;

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium (II) 1,4-diphenyl-1,3-butadiene;

dichloro(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium;

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium dimethyl;

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium bis(trimethylsilylmethyl);

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium (dimethylsilylene)bis(methylene);

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium (III) 2-(N,N-dimethylamino)benzyl;

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium (II) 1,4-diphenyl-1,3-butadiene;

dichloro(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium;

(N-(1,1-dimethylethyl)-1,1-di(4-methylphenyl)-1-((1,2,3,3a,7a-η)-2-methyl-4-phenyl -1H-inden-1-yl)silanaminato-(2-)-N-)-titanium dimethyl;

(N-(1,1-dimethylethyl)-1,1-di(4-methylphenyl)-1-((1,2,3,3a,7a-η)-2-methyl-4-phenyl -1H-inden-1-yl)silanaminato-(2-)-N-)-titanium bis(trimethylsilylmethyl);

(N-(1,1-dimethylethyl)-1,1-di(4-methylphenyl)-1-((1,2,3,3a,7a-η)-2-methyl-4-phenyl -1H-inden-1-yl)silanaminato-(2-)-N-)-titanium (dimethylsilylene)bis(methylene);

(N-(1,1-dimethylethyl)-1,1-di(4-methylphenyl)-1-((1,2,3,3a,7a-η)-2-methyl-4-phenyl -1H-inden-1-yl)silanaminato-(2-)-N-)-titanium (III) 2-(N,N-dimethylamino)benzyl;

(N-(1,1-dimethylethyl)-1,1-di(4-methylphenyl)-1-((1,2,3,3a,7a-η)-2-methyl-4-phenyl -1H-inden-1-yl)silanaminato-(2-)-N-)-titanium (II) 1,4-diphenyl-1,3-butadiene;

dichloro(N-(cyclohexyl)-1,1-di(4-methylphenyl)-1-((1,2,3,3a,7a-η)-2-methyl-4-phenyl-1H-inden-1-yl)silanaminato-(2-)-N-)-titanium;

(N-(cyclohexyl)-1,1-di(4-methylphenyl)-1-((1,2,3,3a,7a-η)-2-methyl-4-phenyl-1H-inden-1-yl)silanaminato-(2-)-N-)-titanium dimethyl;

(N-(cyclohexyl)-1,1-di(4-methylphenyl)-1-((1,2,3,3a,7a-η)-2-methyl-4-phenyl-1H-inden-1-yl)silanaminato-(2-)-N-)-titanium bis(trimethylsilylmethyl);

(N-(cyclohexyl)-1,1-di(4-methylphenyl)-1-((1,2,3,3a,7a-η)-2-methyl-4-phenyl-1H-inden-1-yl)silanaminato-(2-)-N-)-titanium (dimethylsilylene)bis(methylene);

(N-(cyclohexyl)-1,1-di(4-methylphenyl)-1-((1,2,3,3a,7a-η)-2-methyl-4-phenyl-1H-inden-1-yl)silanaminato-(2-)-N-)-titanium (III) 2-(N,N-dimethylamino)benzyl; and (N-(cyclohexyl)-1,1-di(4-methylphenyl)-1-((1,2,3,3a,7a-η)-2-methyl-4-phenyl-1H-inden-1-yl)silanaminato-(2-)-N-)-titanium (II) 1,4-diphenyl-1,3-butadiene.

EXAMPLES

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of about 20–25° C., and "mixed alkanes" refers to a mixture of hydrogenated propylene oligomers, mostly $C_6$–$C_{12}$ isoalkanes, available commercially under the trademark Isopar E™ from Exxon Chemicals Inc. HRMS refers to high resolution mass spectroscopy.

All solvents were purified using the technique disclosed by Pangborn et al, *Organometallics*, 15, 1518–1520, (1996). All compounds, solutions, and reactions were handled under an inert atmosphere (dry box). $^1$H and $^{13}$C NMR shifts were referenced to internal solvent resonances and are reported relative to TMS.

X-ray analysis was performed in the following manner:

Data Collection: A single crystal of suitable dimensions was immersed in oil, Paratone N™, available from Exxon Chemicals, Inc., and mounted on a thin glass fiber. The crystal was transferred to a Bruker SMART PLATFORM diffractometer equipped with a graphite monochromatic crystal, a MoKα radiation source (λ=0.71073 Å), and a CCD (charge coupled device) area detector. The crystal was bathed in a cold nitrogen stream for the duration of data collection (−100° C.).

Program SMART (available from Bruker AXS, Inc., Madison, Wis., USA) was used for diffractometer control, frame scans, indexing, orientation matrix calculations, least squares refinement of cell parameters, crystal faces measurements and the actual data collection. Program ASTRO (available from Bruker AXS, Inc., Madison, Wis., USA) was used to set up data collection strategy.

Raw data frames were read by. program SAINT (available from Bruker AXS, Inc., Madison, Wis., USA) and integrated using 3D profiling algorithms. The resulting data were reduced to produce hkl reflections and their intensities and estimated standard deviations. The data were corrected for Lorentz and polarization effects. Sufficient reflections were collected to represent a range of 1.51 to 2.16 redundancy level with an $R_{sym}$ value range of 2.5 percent, at the lowest 2θ shell of reflections, to 3.0 percent at the highest 2θ shell of reflections (550). Crystal decay correction was applied and was less than 1 percent. The unit cell parameters were refined by least squares of the setting angles of the reflections.

Absorption corrections were applied by integration based on indexed measured faces. Data preparation was carried out using program XPREP (available from Bruker AXS, Inc., Madison, Wis., USA). The structure was solved by direct methods in SHELXTL5.1 (available from Bruker AXS, Inc., Madison, Wis., USA) from which the positions of all of the non-H atoms were obtained. The structure was refined, also in SHELXTL5.1, using full-matrix least-squares refinement. The non-H atoms were refined with anisotropic thermal parameters and all of the H atoms were calculated in idealized positions and refined riding on their parent atoms, or were obtained from a Difference Fourier map and refined without any constraints. A correction for secondary extinction was not applied. The final refinement was carried out using $F^2$ rather than F values. $R_1$ is calculated to provide a reference to the conventional R value but its function is not minimized. Additionally, $wR_2$ is the function that is minimized, and not $R_1$.

The linear absorption coefficient, atomic scattering factors and anomalous-dispersion corrections were calculated from values from the International Tables for X-ray Crystallography (1974). Vol. IV, p. 55. Birmingham: Kynoch Press (Present distributor, D. Reidel, Dordrecht.).

Relevant functions:

$$R_1 = \Sigma(||F_o|-|F_c||)/\Sigma|F_o|$$

$$wR_2 = [\Sigma[w(F_o^2-F_c^2)^2]/\Sigma[wF_o^2{}^2]]^{1/2}$$

$$R_{int.} = \Sigma|F_o^2-F_o^2(\text{mean})|^2/\Sigma[F_o^2]$$

$$S = [\Sigma[w(F_o^2-F_c^2)^2]/(n-p)]^{1/2}$$

where n is the number of reflections and p is the total number of parameters refined $$w=1/[\sigma^2(F_o^2)+(0.0370*p)^2+0.31*p], \quad p=[\max(F_o^2, 0)+2*F_c^2]/3$$

Example 1

Preparation of dichloro(N-(1,1-dimethylethyl)-1,1-di (p-tolyl)-1-((1,2,3,3a,7a-η)-3-(1,3-dihydro-2H-isoindol-2-yl)-1H-inden-1-yl)silanaminato-(2-)-N-)-titanium

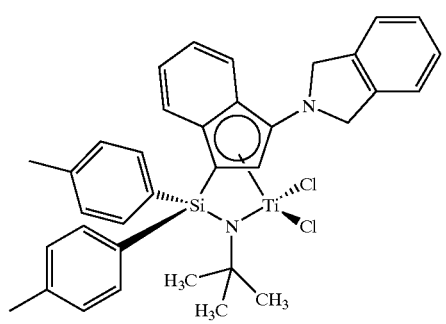

(A) Preparation of N-(tert-butyl)-N-(1,1-p-tolyl)-1-(3-(1, 3-dihydro-2H-isoindol-2-yl)-1H-indenyl)silyl)amine

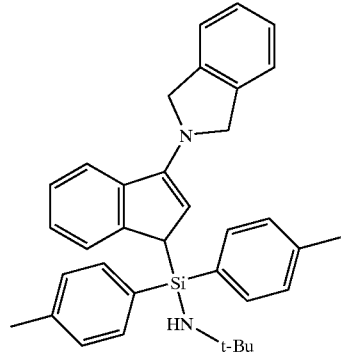

To a 1.70 g (5.35 mmol) of N-(tert-butyl)-N-(1-chloro-1, 1-di(3-p-tolyl)silylamine dissolved in 20 mL of THF was added 1.279 g (5.35 mmol) of 1-(1H-3-indenyl)-1-(2,3-dihydro-1H-isoindolinyl) lithium salt dissolved in 20 mL of THF. After the reaction mixture was stirred for 9 h and then solvent was removed under reduced pressure. The residue was extracted with 40 mL of hexane and filtered. Solvent was removed under reduced pressure giving 2.806 of product as a gray solid. Yield 101.9 percent.

$^1$H($C_6D_6$) δ: 1.10 (s, 9H), 2.01 (s, 3H), 2.08 (s, 3H), 4.12 (d, 1H, $^3J_{H-H}$=1.5 Hz), 4.39 (d, 1H, $^2J_{H-H}$=11.1 Hz), 4.57 (d, 1H, $^2J_{H-H}$=11.7 Hz), 5.55 (d, 1H, $^3J_{H-H}$=2.1 Hz), 6.9–7.22 (m, 10H), 7.56 (d, 1H, $^3J_{H-H}$=7.8 Hz), 7.62 (d, 1H, $^3J_{H-H}$=6.9 Hz), 7.67 (d, 1H, $^3J_{H-H}$=7.8 Hz), 7.83 (d, 1H, $^3J_{H-H}$=7.8 Hz). $^{13}$C{$^1$H} ($C_6D_6$) δ: 21.37, 21.43, 33.78, 41.09, 50.05, 56.56, 104.28, 120.98, 122.46, 123.84, 124.71, 124.84, 126.98, 128.29, 128.52, 129.05, 132.99, 133.68, 135.08, 135.90, 136.01, 138.89, 139.05, 139.09, 141.27, 146.39, 148.48.

(B) Preparation of N-(tert-butyl)-N-(1,1-p-tolyl)-1-(1,3-dihydro-2H-isoindol-2-yl)-1H-indenyl)silyl)amin dilithium salt To a 50 mL hexane solution containing 2.726 g (5.61 mmol) of the N-(tert-butyl)-N-(1,1-p-tolyl)-1-(3-(1,3-dihydro-2H-isoindol-2-yl)-1H-indenyl)silyl)amine was added 7.4 mL of 1.6 M n-BuLi solution. During addition of the n-BuLi, a yellow precipitate appeared. After stirring for 6 h, the yellow precipitate was collected on a frit, washed with 2×25 mL of hexane, and dried under reduced pressure to give 2.262 g of the product as a yellow powder. Yield was 76.6 percent.

$^1$H($C_6D_6$) δ: 1.17 (s, 9H), 2.30 (s, 6H), 4.51 (s, 4H), 6.21 (s, 1H), 6.47 (m, 2H), 6.97 (d, 4H, $^3J_{H-H}$=8.1 Hz), 7.15 (m, 2H), 7.23 (m, 2H), 7.50 (m, 1H), 7.81 (d, 4H, $^3J_{H-H}$=7.8 Hz), 8.07 (d, 1H, $^3J_{H-H}$=7.2 Hz). $^{13}$C{$^1$H} ($C_6D_6$) δ: 21.65, 38.83, 52.46, 59.82, 95.33, 112.93, 114.15, 115.78, 118.29, 122.05, 122.60, 124.16, 124.78, 126.94, 127.30, 133.06, 134.75, 137.30, 141.98, 148.17.

(C) Preparation of dichloro(N-(1,1-dimethylethyl)-1,1-di-p-tolyl-1-((1,2,3,3a,7a-η)-3-(1,3-dihydro-2H-isoindol-2-yl)-1H-inden-1-yl)silanaminato-(2-)-N-)titanium In the drybox 1.552 g (4.19 mmol) of TiCl$_3$(THF)$_3$ was suspended in 20 mL of THF. To this solution, 2.206 g (4.19 mmol) of N-(tert-butyl)-N-(1,1-p-tolyl)-1-(1,3-dihydro-2H-isoindol-2-yl)-1H-indenyl)silyl)amine, dilithium salt dissolved in 30 mL of THF was added within 1 min. The solution was then stirred for 60 min. After this time, 0.76 g of PbCl$_2$ (2.75 mmol) was added and the solution was stirred for 60 min. The THF was then removed under reduced pressure. The residue was first extracted with 60 mL of methylene chloride and filtered. Solvent was removed under reduced pressure leaving a black crystalline solid. Hexane was added (30 mL) and the black suspension was stirred for 10 hour. The solids were collected on a frit, washed with 30 mL of hexane and dried under reduced pressure to give 2.23 g of the desired product as a deep purple solid. Yield was 88.2 percent.

$^1$H (THF-d$_8$) δ: 1.40 (s, 9H), 2.46 (s, 3H), 2.48 (s, 3H), 5.07 (d, 2H, $^2J_{H-H}$=12.3 Hz), 5.45 (d, 2H, $^2J_{H-H}$=12.6 Hz), 5.93 (s, 1H), 6.95 (d, 1H, $^3J_{H-H}$=9.0 Hz), 7.08 (d, 1H, $^3J_{H-H}$=7.8 Hz), 7.15–7.4 (m, 9H), 7.76 (d, 1H, $^3J_{H-H}$=7.8 Hz), 7.82 (d, 1H, $^3J_{H-H}$=7.5 Hz), 8.05 (d, 1H, $^3J_{H-H}$=8.7 Hz). $^{13}$C{$^1$H} (THF-d$_8$) δ: 21.71, 21.76, 33.38, 56.87, 61.41, 94.5, 107.95, 122.86, 125.77, 126.68, 127.84, 127.92, 128.40, 128.49, 129.36, 129.79, 131.23, 131.29, 135.79, 136.43, 136.73, 141.02, 141.22, 150.14.

Example 2

Preparation of(N-(1,1-dimethylethyl)-1,1-di-p-tolyl-1-((1,2,3,3a,7a-η)-3-(1,3-dihydro-2H-isoindol-2-yl)-1H-inden-1-yl)silanaminato-(2-)-N-)dimethyltitanium

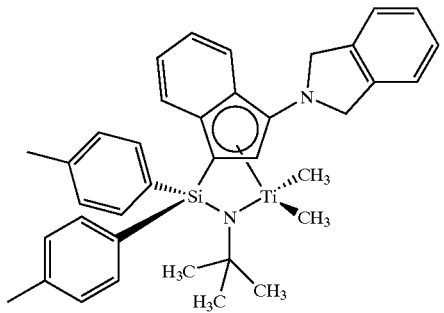

In the drybox 0.50 g of dichloro(N-(1,1-dimethylethyl)-1,1-di-p-tolyl-1-((1,2,3,3a,7a-η)-3-(1,3-dihydro-2H-isoindol-2-yl)-1H-inden-1-yl)silanaminato-(2-)-N-)titanium complex (0.79 mmol) was dissolved in 30 mL of diethyl ether. To this solution, 1.14 mL (1.6 mmol) of MeLi (1.6 M in ether) was added dropwise while stirring over a 1 minute period. After the addition of MeLi was completed, the solution was stirred for 1.5 hour. Diethyl ether was removed under reduced pressure and the residue extracted with 45 mL of hexane. Hexane was removed under reduced pressure giving a red crystalline material. This solid was dissolved in about 7 mL of toluene and 25 mL of hexane, filtered, and the solution was put into the freezer (−27° C.) for 2 days. The solvent was then decanted and the resulting crystals were washed with cold hexane and dried under reduced pressure to give 156 mg of product. Yield was 33.3 percent $^1$H(C$_6$D$_6$) δ: 0.25 (s, 3H), 0.99 (3H), 1.72 (s, 9H), 2.12 (s, 3H), 2.15 (s, 3H), 4.53 (d, 2H, $^2J_{H-H}$=11.7 Hz), 4.83 (d, 2H, $^2J_{H-H}$=11.7 Hz), 5.68 (s, 1H), 6.72 (dd, 1H, $^3J_{H-H}$=8.6 Hz, $^3J_{H-H}$=6.6 Hz), 6.9–7.2 (m, 11H), 7.30 (d, 1H, $^3J_{H-H}$=8.6 Hz).7.71 (d, 1H, $^3J_{H-H}$=8.5 Hz), 7.93 (d, 1H, $^3J_{H-H}$=7.8 Hz), 8.11 (d, 1H, $^3J_{H-H}$=7.8 Hz). $^{13}$C{$^1$H} (C$_6$D$_6$) δ: 21.45, 21.52, 35.30, 50.83, 56.03, 56.66, 57.65, 83.80, 105.64, 122.69, 124.51, 124.56, 125.06, 125.35, 127.33, 128.98, 129.06, 129.22, 133.51, 134.02, 134.62, 136.49, 136.84, 137.69, 139.72, 139.87, 143.84.

Example 3

Preparation of dichloro(N-1,1-dimethylethyl)-1,1-(4-butyl-phenyl)-1-((1,2,3,3a,7a-η)-3-(1,3-dihydro-2H-isoindol-2-yl)-1H-inden-1-yl)silanaminato-(2-)-N-)titanium

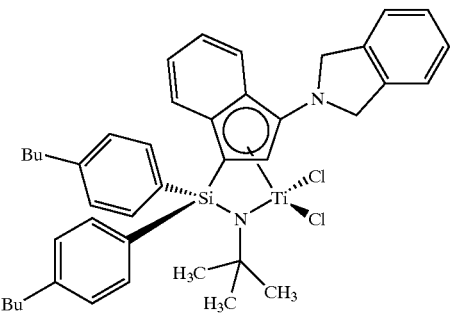

A) Tetramethylsilane[MgCl]$_2$(THF)$_6$

To 40 mL diethyl ether solution of 2.5 g, 15.9 mmol of Me$_2$Si(CH$_2$Cl)$_2$ was added 0.851 g, 35.0 mmol of Mg turnings. After stirring overnight, a large amount of white solid was visible. Solvent was removed under reduced pressure and replaced with 40 mL of tetrahydrofuran (THF). Upon addition of THF, all of the white solid dissolved. After stirring an additional 24 h., about 20 mL of hexane was added and the solution was filtered. The filtrate was put into a freezer (−27° C.) overnight. Solvent was decanted and large colorless crystals were washed with cold hexane (2×20 mL). The solid was then dried under reduced pressure to give 2.753 g of product as the THF hexa-adduct. Yield was 27.1 percent $^1$H NMR (THF-d$_8$): δ−1.81 (s, 4H), −0.21 (s, 6H), 1.77 (m, 28H, THF), 3.66 (m, 28H, THF). $^{13}$C{$^1$H} NMR (THF-d$_8$): δ −2.50, 9.14, 26.37 (THF), 68.46 (THF).

B) dichloro(N-(1,1-dimethylethyl)-1,1-di(4-methylphenyl)-1-((1,2,3,3a,7a-η)-3-(1,3-dihydro-2H-isoindol-2-yl)-1H-inden-1-yl)silanaminato-(2-)-N-)titanium i) Preparation of (p-Bu-Ph)$_2$SiCl$_2$.

To a three-necked 250 mL round-bottom flask under a nitrogen atmosphere equipped with a reflux condenser and a 250 mL dropping funnel 4.87 g of Mg turnings (0.200 moles) were introduced. 1-bromo-4-butyl benzene (42.6 g, 0.200 moles) and 80 mL of THF were then added to the dropping funnel. At this time 10 mL of the bromobenzene/THF solution was added to the Mg turnings with a small amount of ethyl bromide. The solution was then stirred until initiation occurred. The rest of the bromo benzene/THF solution was then added dropwise to allow refluxing to occur. After addition of the bromo benzene/THF solution, the mixture was heated at reflux until the magnesium was consumed.

The resulting Grignard solution was then transferred to a 250 mL dropping funnel which was attached to a three-necked 250 mL round-bottom flask under a nitrogen atmosphere equipped with a reflux condenser. To the round bottomed flask, 100 mL of heptane was introduced followed by SiCl$_4$ (15.3 g, 0.090 moles). To this solution, the Grignard solution was added dropwise. After addition was complete the resulting mixture was refluxed for 2 h and then allowed to cool to room temperature. Under an inert atmosphere the solution was filtered. The remaining salts were further washed with heptane (3×40 mL), filtered and combined with the original heptane solution.

The heptane was then removed via distillation at atmospheric pressure. The resulting viscous oil was then vacuum distilled with collection of the product at 1 mm Hg, (133 Pa) at 210° C. giving 19.3 g (58 percent) of the desired product.

ii) Preparation of bis(4-n-butylphenyl)(t-butylamido)chlorosilane

Dichloro-di(4-n-butylphenyl)silane (4.572 g, 12.51 mmol) was dissolved in 45 mL of methylene chloride. To this solution was added 1.83 g, 25.03 mmol of t-BuNH$_2$. After stirring overnight, the solvent was removed under reduced pressure. The residue was extracted with 45 mL of hexane and filtered. Solvent was removed under reduced pressure leaving 4.852 g of the desired product.

iii) Preparation of (4-n-Bu-Ph)$_2$Si(3-isoindolino-indenyl)(NH-t-Bu)

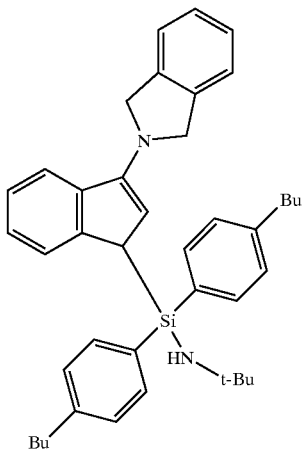

To a 4.612 g (11.47 mmol) of (4-n-Bu-Ph)$_2$Si(Cl)(NH-t-Bu) dissolved in 20 mL of THF was added 2.744 g (8.37 mmol) of lithium 1-isoindolino-indenide dissolved in 30 mL of THF. After the reaction mixture was stirred overnight solvent was removed under reduced pressure. The residue was extracted with 50 mL of hexane and filtered. Solvent removal gave 6.870 g of product as a very viscous red-brown oil. Yield was 91.0 percent.

iv) Preparation of dilithium salt of (4-n-Bu-Ph)$_2$Si(3-isoindolino-indenyl)(NH-t-Bu)

To a 50 mL of hexane solution containing 6.186 g (10.33 mmol) of (4-n-Bu-Ph)$_2$Si(3-isoindolino-indenyl)(NH-t-Bu) was added 13.5 mL of 1.6 M n-BuLi solution. A few minutes after n-BuLi addition, a yellow precipitate appeared. After stirring overnight, the yellow precipitate was collected on the frit, washed with 4×20 mL of hexane and dried under reduced pressure to give 4.42 g of the desired product as a yellow powder. Yield was 70.0 percent.

v) Preparation of dichloro(N-1,1-dimethylethyl)-1,1-(4-butyl-phenyl)-1-((1,2,3,3a,7a-η)-3-(1,3-dihydro-2H-isoindol-2-yl)-1H-inden-1-yl)silanaminato-(2-)-N-)-titanium In the drybox, 2.62 g (7.10 mmol) of TiCl$_3$(THF)$_3$ was suspended in 40 mL of THF. To this solution, 4.32 g (7.07 mmol) of dilithium salt of (4-n-Bu-Ph)$_2$Si(3-isoindolino-indenyl)(NH-t-Bu) dissolved in 60 mL of THF was added within 2 minutes. The solution was then stirred for 60 minutes. After this time, 1.28 g of PbCl$_2$ (4.60 mmol) was added and the solution was stirred for 60 minutes. The THF was then removed under reduced pressure. The residue was extracted with 50 mL of toluene and filtered. Solvent was removed under reduced pressure leaving a black crystalline solid. Hexane was added (35 mL) and the black suspension was stirred for 0.5 hour. The solids were collected on the frit, washed with 2×30 mL of hexane and dried under reduced pressure to give 4.68 g of the desired product as a black-blue, crystalline solid. Yield was 92.4 percent.

Example 4

Preparation of (N-1,1-dimethylethyl)-1,1-(4-n-butylphenyl)-1-((1,2,3,3a,7a-η)-3-(1,3-dihydro-2H-isoindol-2-yl)-1H-inden-1-yl)silanaminato-(2-)-N-)-dimethyltitanium

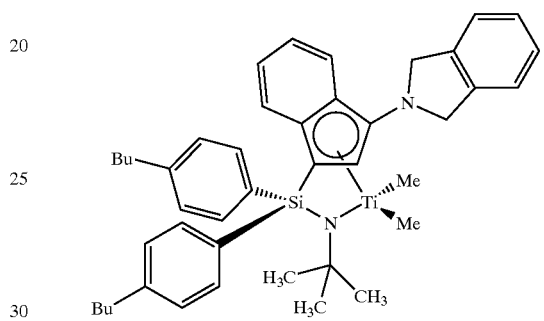

Dichloro(N-1,1-dimethylethyl)-1,1-(4-n-butylphenyl)-1-((1,2,3,3a,7a-η)-3-(1,3-dihydro-2H-isoindol-2-yl)-1H-inden-1-yl)silanaminato-(2-)-N-)titanium (1.61 g, 2.25 mmol, Example 14) was suspended in 35 mL of toluene. To this suspension was added 3 mL (4.75 mmol) of 1.6 M MeLi ether solution. The reaction color changed at once from dark green-black to dark red. After stirring for 1 hour, the solvent was removed under reduced pressure. The residue was extracted with 55 mL of hexane and filtered. Solvent was removed leaving 1.46 g of the desired product as a red solid.

Example 5

Preparation of (N-1,1-dimethylethyl)-1,1-(4-n-butylphenyl)-1-((1,2,3,3a,7a-η)-3-(1,3-dihydro-2H-isoindol-2-yl)-1H-inden-1-yl)silanaminato-(2-)-N-)-titanium (II) 1,3-pentadiene

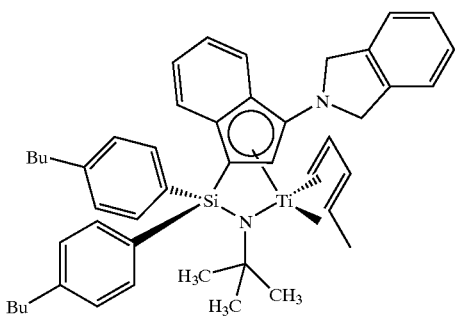

Dichloro(N-1,1-dimethylethyl)-1,1-(4-butyl-phenyl)-1-((1,2,3,3a,7a-η)-3-(1,3-dihydro-2H-isoindol-2-yl)-1H- inden-1-yl)silanaminato-(2-)-N-)titanium (1.266 g, 1.77 mmol, Example 14) was suspended in 60 mL of hexane. The mixture was brought to gentle reflux and then 0.9 mL (0.89 mmol) of piperylene was added followed by 1.86 mL (3.72 mmol) of BrMgBu (2 M in THF). The reaction mixture was refluxed for 2.5 hour. After cooling to room temperature the solution was filtered and solvent was removed under reduced pressure leaving 1.30 g of the desired product as a black glassy solid.

Example 6

Preparation of (N-(1,1-dimethylethyl)-1,1-di(4-n-butylphenyl)-1-((1,2,3,3a,7a-η)-3-(1,3-dihydro-2H-isoindol-2-yl)-1H-inden-1-yl)silanaminato-(2-)-N-) - [(dimethylsilylene)bis(methylene)]titanium

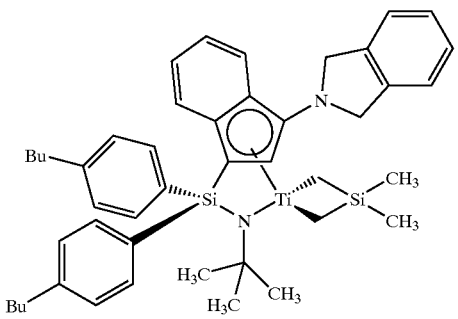

To a 50 mL toluene solution containing 2.33 g, (3.26 mmol) of dichloro(N-(1,1-dimethylethyl)-1,1-di(4-n-butylphenyl)-1-((1,2,3,3a,7a-η)-3-(1,3-dihydro-2H-isoindol-2-yl)-1H-inden-1-yl)silanaminato-(2-)-N-)titanium (Example 14) was added 3.62 g, 4.23 mmol of $Me_2Si(CH_2MgCl)_2$ $(THF)_9$ as a solid. After stirring overnight at room temperature, the solution color changed from green-black to red. Solvent was removed under reduced pressure. The residue was extracted with 40 mL of hexane and filtered. The solvent was removed under reduced pressure to give a red glassy solid. This material was dissolved in 40 mL of hexane and filtered thought a fine frit. Solvent removal gave 2.16 g of product as a red glassy solid. Yield was 89.0 percent.

$^1H$ NMR $(C_6D_6)$: δ 0.03 (s, 3H), 0.44 (s, 3H), 0.62 (d, 1H, $^2J_{H-H}$=7.9 Hz), 1.24 (m, 4H), 1.52 (m, 4H), 1.54 (s, 9H), 2.34 (s, 2H), 2.45 (d, 1H, $^2J_{H-H}$=13.4 Hz), 2.52 (t, 4H, $^3J_{H-H}$=7.8 Hz), 4.61 (m, 4H), 5.84 (s, 1H), 6.74 (t, 1H, $^3J_{H-H}$=7.7 Hz), 6.89 (d, 1H, $^3J_{H-H}$=8.7 Hz), 6.94 (m, 2H), 7.05 (m, 2H), 7.15 (d, 2H, $^3J_{H-H}$=7.5 Hz), 7.26 (d, 2H$^{13}$ $J_{H-H}$=7.8 Hz), 7.31 (d, 1H, $^3J_{H-H}$=9.0 Hz), 7.57 (d, 1H, $^3J_{H-H}$=8.7 Hz), 8.13 (d, 2H, $^3J_{H-H}$=7.8 Hz), 8.17 (d, 2H, $^3J_{H-H}$=7.8 Hz). $^{13}C\{^1H\}$ NMR $(C_6D_6)$: δ −1.08, −0.28, 14.11, 14.15, 33.70, 33.78, 35.91, 36.06, 56.63, 56.88, 80.31, 84.35, 85.24, 103.81, 122.61, 122.81, 122.82, 124.27, 124.36, 127.34, 128.47, 128.51, 129.72, 131.03, 134.87, 135.00, 136.66, 137.16, 137.79, 143.36, 144.66, 144.85. HRMS (EI): calculated for $C_{39}H_{46}N_2Si_2Ti$ (M)$^+$ 646.2679. found 646.2640.

Analysis: Calculated for $C_{39}H_{46}N_2Si_2Ti$: C, 72.42; H, 7.17; N, 4.33. Found: C, 72.78; H, 7.53; N, 4.13.

Example 7

Preparation of (N-1,1-dimethylethyl)-1,1-(4-methylphenyl)-1-((1,2,3,3a,7a-η)-3-(1,3-dihydro-2H-isoindol-2-yl)-,H-inden-1-yl)silanaminato-(2-)-N-)-bis[(trimethylsilyl)methyl]-titanium

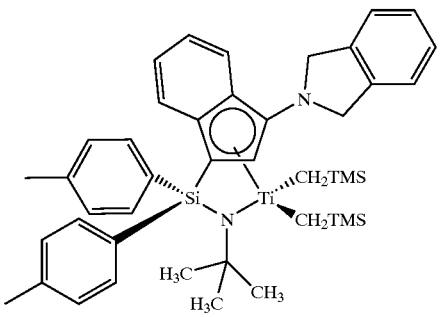

In the drybox 3.42 g of dichloro(N-1,1-dimethylethyl)-1,1-(4-methylphenyl)-1-((1,2,3,3a,7a-η)-3-(1,3-dihydro-2H-isoindol-2-yl)-1H-inden-1-yl)silanaminato-(2-)-N-)titanium (5.42 mmol) (prepared substantially according to example 5) was partly dissolved in 70 mL of toluene. To this solution 11.6 mL (11.6 mmol) of $LiCH_2TMS$ (1 M in pentane) was added dropwise while stirring over a one minute period. After the addition of lithium reagent was completed, the solution was stirred for 15 hours at room temperature. The reaction mixture was filtered and solvent was removed under reduced pressure. The resulting solid was dissolved in 15 mL of toluene followed by addition of 45 mL of hexane. The solution was filtered and solvent removed under reduced pressure leaving a red-brown crystalline solid. Hexane was added (25 mL) and the mixture was stirred for 10 min. and then put into freezer for 24 hours. Red crystalline solid was collected by filtration, washed with 2×8 mL of cold hexane, and then dried under reduced pressure to give 2.722 g of the desired product.

$^1H$ NMR $(C_6D_6)$: δ −0.67 (d, 2H, $^2J_{H-H}$=11.7 Hz, —$CH_2Si(CH_3)_3$), 0.14 (s, 9H, —$CH_2Si(CH_3)_3$), 0.20 (s, 9H, —$CH_2Si(CH_3)_3$), 1.10 (d, 2H, $^2J_{H-H}$=12.0 Hz, —$CH_2Si$ $(CH_3)_3$), 1.31 (m, 2H, —$CH_2Si(CH_3)_3$), 1.71 (s, 9H, $C(CH_3)_3$), 2.13 (s, 6H), 4.77 (d, 2H, $^2J_{H-H}$=12.0 Hz), 4.91 (d, 2H, $^2J_{H-H}$=12.0 Hz), 5.78 (s, 1H), 6.73 (t, 1H, $^3J_{H-H}$=7.7 Hz), 6.98 (m, 3H), 7.05 (m, 2H), 7.13 (d, 2H, $^3J_{H-H}$=7.8 Hz), 7.20 (d, 2H, $^3J_{H-H}$=7.8 Hz), 7.33 (d, 1H, $^3J_{H-H}$=8.4 Hz), 7.78 (d, 1H, $^3J_{H-H}$=90 Hz), 7.98 (d, 2H, $^3J_{H-H}$=7.5 Hz), 8.06 (d, 2H, $^3J_{H-H}$=7.8 Hz). $^{13}C\{^1H\}$ NMR $(C_6D_6)$: δ 2.74, 3.52, 21.47, 21.50, 35.33, 57.03, 58.74, 69.08, 80.50, 84.92, 102.34, 122.57, 124.42, 124.78, 124.92, 125.12, 127.55, 128.92, 129.09, 129.49, 133.99, 134.30, 134.60, 136.65, 137.09, 137.43, 139.72, 139.83, 146.11. HRMS (EI): calculated for $C_{43}H_{58}N_2Si_3Ti$ (M)$^+$735.3465, found 735.3461. Analysis Calculated for $C_{43}H_{58}N_2Si_3Ti$: C, 70.26; H, 7.95; N, 3.81. Found: C, 65.96; H, 8.74; N, 2.11.

The X-ray structure (ORTEP) for the compound is provided in FIG. 1.

Example 8

Preparation of (N-(1,1-dimethylethyl)-1,1-di(4-methylphenyl)-1-((1,2,3,3a,7a-η)-3-(1,3-dihydro-2H-isoindol-2-yl)-1H-inden-1-yl)silanaminato-(2-)-N-)-[(dimethylsilylene)bis(methylene)]titanium

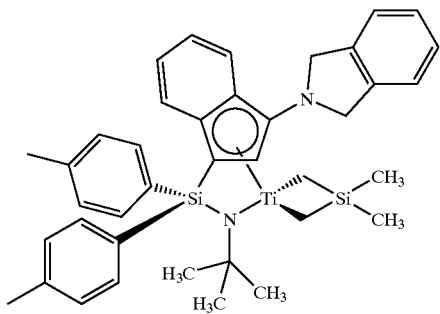

A) Tetramethylsilane[MgCl]$_2$(THF)$_6$

To 40 mL diethyl ether solution of 2.5 g, 15.9 mmol of Me$_2$Si(CH$_2$Cl)$_2$ was added 0.851 g, 35.0 mmol of Mg turnings. After stirring overnight large amount of white solid was visible. Solvent was removed under reduced pressure and replaced with 40 mL of tetrahydrofuran (THF). Upon addition of THF all of the white solid dissolved. After stirring an additional 24 hr, about 20 mL of hexane was added and the solution was filtered. The filtrate was put into a freezer (−27° C.) overnight. Solvent was decanted and large colorless crystals were washed with cold hexane (2×20 mL). The solid was then dried under reduced pressure to give 2.753 g of product as the THF hexa-adduct. Yield was 27.1 percent.

$^1$H NMR (THF-d$_8$): δ −1.81 (s, 4H), −0.21 (s, 6H), 1.77 (m, 28H, THF), 3.66 (m, 28H, THF). $^{13}$C{$^1$H} NMR (THF-d$_8$): δ −2.50, 9.14, 26.37 (THF), 68.46 (THF).

B) Preparation of (N-(1,1-dimethylethyl)-1,1-di(4-methylphenyl)-1-((1,2,3,3a,7a-η)-3-(1,3-dihydro-2H-isoindol-2-yl)-1H-inden-1-yl)silanaminato-(2-)-N-)-[(dimethylsilylene)bis-(methylene)]titanium To a 50 mL toluene solution containing 0.60 g, 0.95 mmol of dichloro(N-(1,1-dimethylethyl)-1,1-di(4-methyl-phenyl)-1-((1,2,3,3a,7a-η)-3-(1,3-dihydro-2H-isoindol-2-yl)-1H-inden-1-yl)silanaminato-(2-)-N-)titanium (prepared substantially according to the technique of Example 5) was added 0.667 g, 1.05 mmol of Me$_2$Si(CH$_2$MgCl)$_2$(THF)$_6$ as a solid. After stirring for 2 hours at room temperature, proton NMR analysis showed about 70 percent conversion to the product. After stirring an additional 2 days, the $^1$H NMR spectrum did not change. An additional 0.25 g of the diGrigniard was added. Within minutes the reaction mixture turned from green-yellow to red. After stirring an additional 6 hours, the solvent was removed under reduced pressure. The residue was extracted with 40 mL of hexane and filtered. Solvent was removed under reduced pressure to give a red glassy solid. This solid was dissolved back in 15 mL of hexane. After standing at room temperature overnight, the solvent was decanted and red crystals were washed with cold hexane (2×2 mL). These crystals were dried under reduced pressure to give 0.448 g of the desired product. Yield was 72.9 percent.

$^1$H NMR (C$_6$D$_6$): δ −0.04 (s, 3H), 0.44 (s, 3H), 0.63 (d, 1H, $^2J_{H-H}$=12.9 Hz), 1.52 (s, 9H), 2.15 (s, 6H), 2.34 (m, 2H), 2.45 (d, 1H, $^2J_{H-H}$=12.9 Hz), 4.61 (m, 4H), 5.81 (s, 1H), 6.74 (t, 1H, $^3J_{H-H}$=7.8 Hz), 6.88 (d, 1H, $^3J_{H-H}$=6.6 Hz), 6.92 (m, 2H), 7.05 (m, 2H), 7.15 (d, 2H, $^3J_{H-H}$=8.1 Hz), 7.21 (d, 2H, $^3J_{H-H}$=8.1 Hz), 7.37 (d, 1H, $^3J_{H-H}$=8.4 Hz), 7.56 (d, 1H, $^3J_{H-H}$=8.4 Hz), 8.09 (d, 2H, $^3J_{H-H}$=6.9 Hz), 8.11 (d, 2H, $^3J_{H-H}$=7.2 Hz). $^{13}$C{$^1$H} NMR (C$_6$D$_6$): δ −1.10, −0.30, 21.50, 21.56, 35.87, 56.62, 56.88, 80.27, 84.40, 85.15, 103.75, 122.61, 122.81, 123.83, 124.29, 124.37, 127.35, 129.12, 129.68, 130.98, 134.58, 134.61, 136.65, 137.14, 137.78, 139.66, 139.86, 143.33. HRMS (EI): calculated for C$_{39}$H$_{46}$N$_2$Si$_2$Ti (M)$^+$646.2679, found 646.2640. Analysis: Calculated for C$_{39}$H$_{46}$N$_2$Si$_2$Ti: C, 72.42; H, 7.17; N, 4.33. Found: C, 72.78; H, 7.53; N, 4.13.

Figure 2:
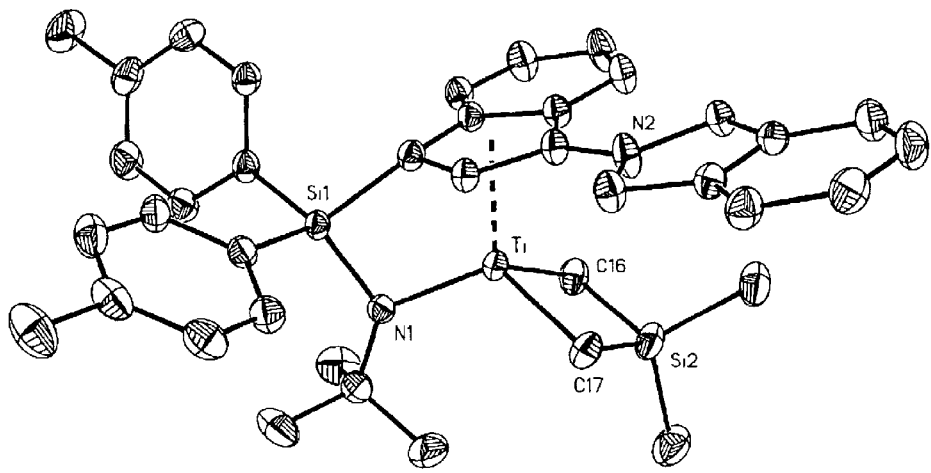
FIG. 2 shows the single crystal structure derived by X-ray analysis (ORTEP) of (N-(1,1-dimethylethyl)-1,1-di(4-methylphenyl)-1-((1,2,3,3a,7a-η)-3-(1,3-dihydro-2H-isoindol-2-yl)-1H-inden-1-yl)silanaminato-(2-)-N-)-titanium bis(trimethylsilylmethyl) (Example 8).

The X-ray structure (ORTEP) for the compound is provided in FIG. 2.

Example 9

Preparation of dichloro(N-(1,1-dimethylethyl)-1,1-di(4-methylphenyl)-1-((1,2,3,3a,7a-η)-3-(1-pyrrolidinyl)-1H-inden-1-yl)silanaminato-(2-)-N-)-titanium

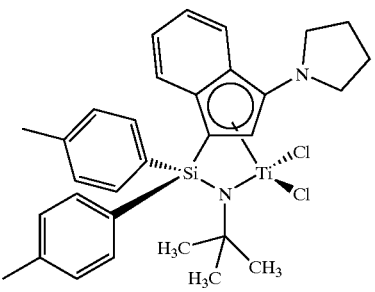

(A) Preparation of N-(tert-butyl)-N-(1-chloro-1,1-di-p-tolylsilyl)amine. To a solution of of 10.0 g (35.6 mmol) of dichloro-p-ditolylsilane in 300 mL of hexane was added 5.20 g (71.1 mmol) of t-butyl amine. The reaction mixture was stirred overnight, then filtered. The hexane was removed under reduced pressure to give the product as a viscous, colorless oil. The yield was 10.83 g (96 percent).

$^1$H(C$_6$D$_6$) δ: 1.12 (s, 9H), 2.04 (s, 6H), 7.01 (d, 4H), 7.82 (d, 2H). $^{13}$C{$^1$H}(C$_6$D$_6$) δ: 21.4, 33.2, 50.80, 129.06, 132.67, 135.09, 140.46.

(B) Preparation of N-(tert-butyl)-N-(1,1-di(4-methylphenyl)-1-(3-tetrahydro-1H-1-pyrrolyl-1H-1-indenyl)silyl)amine. A solution of 1-(1H-3-indenyl) pyrrolidine, lithium salt (1.00 g, 5.23 mmol) in 40 mL of THF was added dropwise to a 80 mL THF solution N-(tert-butyl)-N-(1-chloro-1,1-di-p-tolylsilyl)amine (1.66 g, 5.23 mmol). After the addition was complete the reaction mixture was stirred overnight. The solvent was then removed under reduced pressure. The residue was extracted with hexane and the solution filtered. The solvent was then removed under reduced pressure leaving 2.41 g of product. Yield was 99 percent.

$^1$H(C$_6$D$_6$) δ 1.07 (s, 9H), 1.52 (bs, 4H), 2.04 (s, 3H), 2.09 (s, 3H), 3.00 (bs, 2H), 3.14 (bs, 2H), 4.07 (s, 1H), 5.52 (s, 1H), 7.00–7.84 (m, 12H).

(C) Preparation of N-(tert-butyl)-N-(1,1-di(4-methylphenyl)-1-(3-tetrahydro-1H-1-pyrrolyl-1H-1-indenyl)silyl)amine, dilithium salt. In the drybox, 2.41 g (5.16 mmol) of N-(tert-butyl)-N-(1,1-di(4-methylphenyl)-1-1-(3-tetrahydro-1H-1-pyrrolyl-1H-1-indenyl)silyl)amine was combined with 80 mL of hexane. To this solution, 6.45 mL (10.33 mmol) of n-BuLi (1.6 M in hexanes) was added dropwise. Upon complete addition of the n-BuLi, the solution was stirred overnight. The resulting precipitate was collected via filtration, washed with hexane and dried under reduced pressure to give 1.52 g of product. Yield was 61 percent.

(D) Preparation of dichloro(N-(1,1-dimethylethyl)-1,1-di(4-methylphenyl)-1-((1,2,3,3a,7a-η)-3-(1-pyrrolidinyl)-1H-inden-1-yl)silanaminato-(2-)-N-)-titanium N-(tert-butyl)-N-(1,1-di(4-methylphenyl)-1-(3-tetrahydro-1H-1-pyrrolyl-1H-1-indenyl)silyl)amine, dilithium salt (1.52 g, 3.26 mmol) was added as a solid to a 80 mL solution of THF containing TiCl$_3$(THF)$_3$ (1.21 g 3.26 mmol). After 45 min, PbCl$_2$ (0.45 g, 1.63 mmol) was added as a solid. The reaction mixture was then stirred an additional hour. The solvent was removed under reduced pressure. The residue was extracted with toluene and filtered. Toluene was removed under reduced pressure and the residue was triturated with hexane. The solid was collected by filtration, washed with hexane and then dried under reduced pressure. 1.40 g of product was obtained. Yield was 73 percent.

$^1$H (CDCl$_3$) δ 1.33 (s, 9H), 1.99 (br s, 4H), 2.36 (s, 3H), 2.39 (s 3H), 3.65 (br s, 2H), 3.87 (br s, 2H), 5.74 (s, 11H), 7.10 (m, 11H), 7.25 (bs, 5H), 7.60 (m, 2H), 7.77 (s, 2H) 7.82 (d, 1H). $^{13}$C{$^1$H}(CDCl$_3$) δ: 21.01, 21.68, 25.73, 333.35, 50.70, 60.86, 83.69, 107.91, 125.58, 126.81, 127.23, 127.98, 128.95, 128.99, 129.37, 131.23, 135.48, 136.08, 136.36, 140.33, 140.53, 150.38.

Example 10

Preparation of (N-(1,1-dimethylethyl)-1,1-di(4-methylphenyl)-1-((1,2,3,3a,7a-η)-3-(1-pyrrolidinyl)-1H-inden-1-yl)silanaminato-(2-)-N-) dimethyltitanium

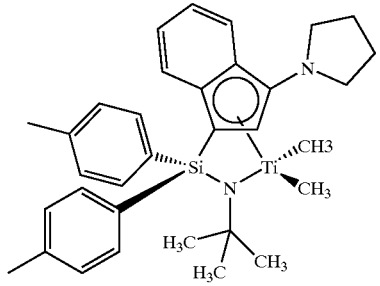

In the drybox 0.444 g dichloro(N-(1,1-dimethylethyl)-1,1-di(4-methylphenyl)-1-((1,2,3,3a,7a-η)-3-(1-pyrrolidinyl)-1H-inden-1-yl)silanaminato-(2-)-N-)titanium complex (0.76 mmol) was dissolved in 30 mL of diethylether. To this solution 1.00 mL (1.6 mmol) of MeLi (1.6 M in ether) was added dropwise while stirring over a 2 minute period. After the addition of MeLi was completed, the solution was stirred for 1.5 hour. Et$_2$O was removed under reduced pressure and the residue extracted with 45 mL of hexane. Hexane was removed under reduced pressure giving 0.348 mg of red, crystalline material. This red solid was dissolved in about 5 mL of hexane (heating was used) and then the vial was put into freezer overnight at −27° C., giving 75 mg of red crystals.

$^1$H(C$_6$D$_6$) δ: 0.26 (s, 3H), 1.01 (s, 3H), 1.44 (m, 4H), 1.72 (s, 9H), 2.01 (s, 3H), 2.14 (s, 3H), 3.12 (m, 2H), 3.36 (m, 2H), 5.60 (s, 11H), 6.70 (ddd, 1H, $^3J_{H-H}$=8.7 Hz, $^3J_{H-H}$=6.6 Hz, $^4J_{H-H}$=0.9 Hz), 6.96 (ddd, 1H, $^3J_{H-H}$=8.6 Hz, $^3J_{H-H}$=6.6 Hz, $^4J_{H-H}$=0.9 Hz), 7.12 (m, 4H), 7.68 (d, 1H, $^3J_{H-H}$=8.7 Hz), 7.68 (d, 1H, $^3J_{H-H}$=9.0 Hz), 7.89 (d, 2H, $^3J_{H-H}$=7.8 Hz), 8.11 (d, 2H, $^3J_{H-H}$=7.8 Hz). $^{13}$C{$^1$H} (C$_6$D$_6$) δ: 21.43, 21.50, 25.82, 35.31, 49.87, 50.45, 55.53, 57.45, 83.28, 105.28, 124.31, 124.86, 125.00, 125.50, 128.86, 128.96, 129.20, 133.65, 134.08, 134.77, 136.46, 136.81, 139.57, 139.76, 144.86.

Example 11

Preparation of (N-(1,1-dimethylethyl)-1,1-di(4-methylphenyl)-1-((1,2,3,3a,7a-η)-2-methyl-3-phenyl-1H-inden-1-yl)silanaminato-(2-)-N-)titanium dichloride

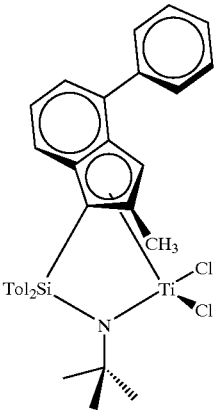

(A) 2-methyl-4-phenyl indenyl lithium In a 400 mL jar were placed 10.6 g (51.4 mmoles) of 2-methyl-4-phenyl indene and 200 mL of hexanes. Then, 33 mL of a 1.6 M hexane solution of butyl lithium (52.4 mmoles) were added at room temperature; the mixture was stirred overnight. The precipitate was filtered and washed with hexane and dried to give 10.60 (97 percent) of a pale yellow solid.

(B) di(tolyl)(t-butylamido)chlorosilane To a vigorously stirred solution of di(p-tolyl)dichlorosilane (7.5 g, 27 mmoles) in 180 mL of hexane, was added a solution of tert-butyl amine in 30 mL of hexane (3.9 g, 53.3 mmoles) over a period of five minutes followed by stirring of the mixture overnight. The mixture was filtered and the filtrate dried under reduced pressure to give 4.7 grams (55 percent yield) of the desired product.

$^1$H NMR (C$_6$D$_6$): δ7.8 (d, 4H), 7.0 (d, 4H), 2.0 (s, 6H), 1.55 (s, 1H), 1.1 (s, 9H). $^{13}$C {$^1$H} NMR(C$_6$D$_6$): δ 140.4, 135.1, 132.7, 129.0, 50.8, 33.2, 21.4.

(C) di(tolyl)(t-butylamido)(triflate)silane To a mixture of 6.4 g (25 mmoles) of silver triflate in 100 mL of acetonitrile was added over a period of five minutes a solution of the di(tolyl)t-butylamidochlorosilane dissolved in 80 mL of acetonitrile. A white precipitate formed immediately. The mixture was stirred for one hour and decanted, after which the volatiles were removed. The residue was treated with hexane, filtered and the volatiles were removed to leave 9.64 g (95 percent yield) of a pale yellow viscous oil.

$^1$H NMR (CDCl$_3$): δ 7.58 (d, 4H), 7.2 (d, 4H), 2.4 (s, 6H), 2.2 (s, 1H), 1.24 (s, 9H); $^{13}$C {$^1$H} NMR (C$_6$D$_6$): δ 141.7, 134.7, 129.1, 127.0, 50.9, 33.0, 21.6; $^{19}$F NMR (CDCl$_3$): −77.0 δ (CCl$_3$F=0 δ).

(D) (2-Methyl-4-phenyl inden-1-yl)-N-(1,1-dimethylethyl) bis(tolyl)silanamine To a mixture of di(tolyl) (t-butylamido)(triflate)silane (9.64 g, 22.3 mmoles) in 60 mL of THF was added a solution of 2-methyl-4-phenylindenyl lithium (5.0 g, 23.5 mmoles; 5 percent molar excess) in 100 mL of THF. The mixture was stirred for one hour at room temperature, the volatiles were removed under reduced pressure, and the residue was extracted with hexanes and filtered. The filtrate was dried in vacuo to give 11.5 g (105 percent) of a very viscous, sticky pale orange oil. THF was still evident by NMR analysis.

(E) (2-Methyl-4-phenylinden-1-yl)-N-(1,1-dimethylethyl)di(tolyl)silanamidetitanium dichloride also referred to as (N-(1,1-dimethylethyl)-1,1-di(4-methylphenyl)-1-((1,2,3,3a,7a-η)-2-methyl-3-phenyl-1H-inden-1-yl)silanaminato-(2-)-N-)titanium dichloride In a 500 mL glass jar were placed 10.76 g (22.0 mmoles) of (2-methyl-4-phenylinden-1-yl)-N-(1,1-dimethylethyl)di(tolyl)silanamine, 300 mL of hexane, and then 28.2 mL of a 1.6 M hexane solution of BuLi (2.04 equiv., 45 mmoles) were added. The mixture was stirred for two hours, about ⅔ of the solvent was removed and then 200 mL of THF were added to the mixture. Then 8.2 g (22.0 mmoles) of $TiCl_3 \cdot 3THF$ was added; the mixture was stirred for thirty minutes, followed by addition of $PbCl_2$ (4.2 g, 1.3 electron equivalents), and 10 mL of $CH_2Cl_2$. After thirty minutes the volatiles were removed in vacuo, the residue repeatedly extracted with hexane, and the extracts filtered. The filtrate was dried to give 5.0 g (37 percent) of a dark orange-red solid.

$^1H$ NMR ($C_6D_6$): δ7.8 (d), 7.6 (d), 7.2 (m), 7.1 (br s), 7.05 (m), 6.8 (m), 2.1 (s, 6H), 1.95 (s, 3H), 1.65 (s, 9H).

Example 12

Preparation of (N-(1,1-dimethylethyl)-1,1-di(4-methylphenyl)-1-((1,2,3,3a,7a-η)-2-methyl-3-phenyl-1H-inden-1-yl)silanaminato-(2-)-N-)titanium dimethyl In a 50 mL jar were placed 0.54 g (0.9 mmoles) of (N-(1,1-dimethylethyl)-1,1-di(4-methylphenyl)-1-((1,2,3,3a,7a-η)-2-methyl-3-phenyl-1H-inden-1-yl)silanaminato-(2-)-N-)titanium dichloride and 20 mL of ether. Then, 0.6 mL of a 3 M diethylether solution of methyl magnesium iodide (1.8 mmoles) were added and the mixture was stirred for one hour. The volatiles were removed under reduced pressure and the residue (0.3 g) was redissolved in hexane, filtered and the filtrate dried again; this process (redissolve-filter-dry) was repeated three times to remove insoluble material. The semi-solid residue was treated with about 0.3 mL of ether, and the ether was quickly removed under reduced pressure to give a brownish-golden glassy solid (0.22 g, 43 precent yield).

$^1H$ NMR ($C_6D_6$): δ 7.9 (d), 7.75 (d), 7.6 (d), 7.2 (m), 7.1 (br s), 7.05 (m), 6.8 (m), 2.1 (s, 3H), 2.08 (s, 3H), 1.8 (s, 3H), 1.75 (s, 9H), 1.0 (s, 3H), 0.2 (s, 3H). $^{13}C$ {$^1H$} NMR ($C_6D_6$): δ 142.9, 141.0, 139.9, 139.5, 138.7, 137.0, 136.0, 135.2, 135.0, 134.5, 131.0, 129.0, 128.9, 128.6, 127.74, 127.67, 127.3, 125.6, 125.4, 116.0, 89.9, 66.5, 57.9, 57.7, 53.4, 35.0, 34.8, 31.8, 25.5, 22.9, 21.4, 20.7, 19.0, 14.2, 13.9.

Ethylene/1-Octene Polymerization Conditions I

All liquid and gas feeds were passed through columns of alumina and a decontaminant (Q5™ catalyst available from Englehardt Chemicals Inc.) prior to introduction into the reactor. Catalyst components are handled in a glovebox containing an atmosphere of argon or nitrogen. A stirred 2.0 liter reactor is charged with about 740 g of mixed alkanes solvent and 118 g of 1-octene comonomer. Hydrogen (25 psi, 170 kPa) is added as a molecular weight control agent by differential pressure expansion from a 75 mL addition tank. The reactor is heated to 140° C. and saturated with ethylene at 500 psig (3.4 MPa). Metal complex as dilute toluene solution and cocatalyst as dilute solutions in toluene or methylcyclohexane, were mixed in a 1:1 molar ratio and transferred to a catalyst addition tank and injected into the reactor. The cocatalyst was methyldi(octadecyl)ammonium tetrakis(pentafluorophenyl)borate, the ammonium cation of which is derived from a mixture of amines available commercially as methyl bis(tallow)amine. The polymerization conditions were maintained for 15 minutes with ethylene added on demand. The resulting solution was removed from the reactor, quenched with isopropyl alcohol, and stabilized by addition of a toluene solution containing about 67 mg/100 g polymer of a hindered phenol antioxidant (Irganox™ 1010 from Ciba Geigy Corporation) and about 133 mg/100 g polymer of a phosphorus stabilizer (Irgafos 168 from Ciba Geigy Corporation).

Between sequential polymerization runs, a wash cycle was conducted in which 850 g of mixed alkanes was added to the reactor and the reactor was heated to 150° C. The reactor was then emptied of the heated solvent immediately before beginning a new polymerization run.

Polymers were recovered by drying in a vacuum oven programmed to reach 140° C. over a period of about 20 hours. Density values are derived by determining the polymer's mass when in air and when immersed in methylethyl ketone. Micro melt index values (MMI) are obtained using a Custom Scientific Instrument Inc. Model CS-127MF-015 apparatus at 190° C., and are unit less values calculated as follows: MMI=1/(0.00343 t–0.00251), where t=time in seconds as measured by the instrument. Results are contained in Table 1.

TABLE 1

| Run | Catalyst (μmol) | Yield (g) | Eff.[1] | Density (g/ml) | Mw (× $10^3$) | Mw/Mn | MMI[2] |
|---|---|---|---|---|---|---|---|
| 1 | Ex. 2 (0.3) | 18.8 | 1.31 | 0.897 | | | <0.1 |
| 2 | Ex. 4 (0.3) | 40.9 | 2.85 | 0.892 | | | <0.1 |
| 3 | Ex. 10 (0.15) | 19.5 | 2.7 | 0.901 | 331 | 1.96 | — |
| 4 | Ex. 10 (0.25) | 46.7 | 3.9 | 0.902 | — | — | <0.1 |
| 5 | Ex 12 (0.40) | 21.1 | 1.1 | 0.874 | 125 | 2.28 | 0.7 |
| A* | DSAT[3] (0.4) | 76.1 | 4.0 | 0.897 | 67 | 2.23 | 8.9 |

[1]efficiency, g polymer/μg titanium
[2]micro melt index 190° C., (comparative technique of melt index determination)
[3]dimethyl(N-(1,1-dimethylethyl)-1,1-dimethyl-1-(2,3,4,5-tetramethyl-cyclopentadienyl)-silanaminato titanium
*comparative, not an example of the invention Ethylene/1-Octene/Ethylidenenorbornene Polymerization Conditions All liquid except ethylidenenorbornene (ENB) and gas feeds were passed through columns of alumina and a decontaminant (Q5™ catalyst available from Englehardt Chemicals Inc.) prior to introduction into the reactor. ENB was passed through a short column (3×10 cm) of alumina prior to introduction to the reactor. Catalyst components are handled in a glovebox containing an atmosphere of argon or nitrogen. A stirred 2.0 liter reactor is charged with about 640 g of mixed alkanes solvent, 150 g of 1-octene and 16 g of ENB. Hydrogen (20 psi, 140 kPa) is added as a molecular weight control agent by differential pressure expansion from a 75 mL addition tank. The reactor is heated to 100° C. and saturated with ethylene at 500 psig (3.5 MPa). Metal complex as dilute toluene solution and cocatalyst as dilute solutions in toluene were mixed in a 1:1 molar ratio and transferred to a catalyst addition tank and injected into the reactor. The cocatalyst was methyldi(octadecyl)ammonium tetrakis(pentafluoro-phenyl)borate, the ammonium cation of which is derived from a mixture of amines available commercially as methyl bis(tallow)amine. The polymerization conditions were maintained for 15 minutes with ethylene added on demand. The resulting solution was removed from the reactor, quenched with isopropyl alcohol, and stabilized by addition of a toluene solution containing about 67 mg/100 g polymer of a hindered phenol antioxidant (Irganox™ 1010 from Ciba Geigy Corporation) and about 133 mg/100 g polymer of a phosphorus stabilizer (Irgafos 168 from Ciba Geigy Corporation).

Between sequential polymerization runs, a wash cycle was conducted in which 850 g of mixed alkanes was added to the reactor and the reactor was heated to 130° C. The reactor was then emptied of the heated solvent immediately before beginning a new polymerization run.

Polymers were recovered by drying in a vacuum oven set at 140° C. for about 20 hours. Density values are derived by determining the polymer's mass when in air and when immersed in methylethyl ketone. GPC results are determined by standard methods and are reported relative to a polystyrene/polyethylene universal calibration. The percent ethylene, octene and ENB for the polymer were determined by $^{13}$C NMR analysis of the material. Results are contained in Table 2.

TABLE 2

| Run | Catalyst (μmol) | Yield (g) | Eff.[1] | Density (g/ml) | Mw (× 10³) | Mw/Mn | Percent octene | Percent ENB |
|---|---|---|---|---|---|---|---|---|
| 6 | Ex. 12 (0.95) | 33.2 | 0.73 | 0.860 | 407 | 2.3 | 41 | 2.5 |
| B* | ID[2] (1.0) | 59.1 | 1.23 | 0.874 | 317 | 2.0 | 33 | 2.8 |

[1]efficiency, g polymer/μg titanium
[2]dimethyl(N-(1,1-dimethylethyl)-1,1-dimethyl-1-(2,3,4,5-tetramethylcyclopentadienyl)-silanaminato titanium
*comparative, not an example of the invention

What is claimed is:

1. A process for polymerizing ethylene, optionally at least one diene, and further optionally a $C_{3-12}$ α-olefin by contactina a mixture thereof with a metal complex and an activating cocatalyst under addition polymerization conditions and covering the resulting polymer product, characterized in that the metal complex is a metal complex corresponding to the formula:

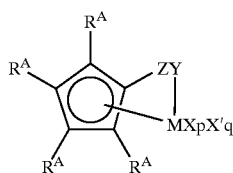

where M is a Group 4 metal that is in the +2, +3 or +4 formal oxidation state;

$R^A$ independently each occurrence is hydrogen, or a hydrocarbyl, balohydrocarbyl, hydrocarbyloxy-hydrocarbyl, dihydrocarbylaminohydrocarbyl, dihydrocarbylamino, hydrocarbyloxy, hydrocarbylsilyl, or trihydrocarbylsilyihydrocarbyl group of from 1 to 80 atoms, not counting hydrogen, or optionally, two or more $R^A$ groups may be covalently linked together; and

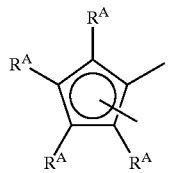

is a 2-alkyl-4-arylinden-1-yl group of up to 30 total carbon toms;

Z is $(R^D)_2Si=$, wherein $R^D$ independently each occurrence is $C_{1-10}$ alkyl substituted phenyl or two $R^D$ groups together are alkyl- or polyalkyl-substituted arylene of up to 40 carbons; and Y is bonded to M and Z and is selected from the group consisting of —O—, —S—, —NR$^E$—, and —PR$^E$—; wherein, $R^E$ independently each occurrence is hydrogen, or a member selected from hydrocarbyl, hydrocarbyloxy, silyl, halogenated alkyl, halogenated aryl, and combinations thereof, said $R^E$ having up to 20 nonhydrogen atoms X is an anionic or dianionic ligand group having up to 60 atoms exclusive of the class of ligands that are cyclic, delocalized, π-bound ligand groups;

X' independently each occurrence is a neutral ligand having up to 40 atoms p is zero or 2, and is two less than the formal oxidation state of M when X is an anionic ligand, and when X is a dianionic ligand group, p is 1; and q is zero, 1 or 2.

2. The process of claim 1 wherein the catalyst composition additionally comprises an activating cocatalyst, wherein the molar ratio of the metal complex to the activating cocatalyst is from 1:10,000 to 100:1.

3. A process according to claim 1 wherein two $R^D$ groups together are alkyl- or polyalkyl-substituted arylene of up to 40 carbons.

4. A process for polymerizing ethylene, at least one diene, and optionally a $C_{3-12}$ α-olefin by contacting a mixture thereof with a metal complex an activating cocatalyst under addition polymerization conditions and recovering the resulting polymer product, characterized in that the metal complex is a metal complex corresoonding to the formula:

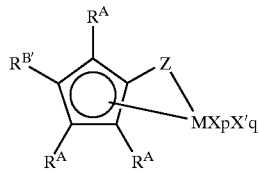

where M is a Group 4 metal that is in the +2, +3 or +4 formal oxidation state;

$R^A$ independently each occurrence is hydrogen, or a hydrocarbyl, halohvydrocarbyl, hydrcocarbyloxy-hydrocabyl, dihydrocarbylaminohydrocarbyl, dihydrocarbylamino, hydrocarbyloxy, hydrocarbylsilyi, or trihydrocarbylsilylhydrocarbyl group of from 1 to 80 atoms, not counting hydrogen, or optionally, two or more $R^A$ groups may be covalently linked together; and

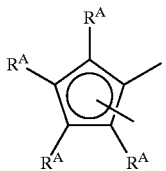

is a 2-alkyl-4-arylinden-1-yl group of up to 30 total carbon atoms;

Z is $(R^D)_2Si=$, wherein $R^D$ independently each occurrence is $C_{1-10}$ alkyl substituted phenyl or two $R^D$ groups together are alkyl- or polyalkyl-substituted arylene of up t 40 carbons; and Y is bonded to M and Z and is selected from the group consistinn of —O—, —S—, —NR$^E$—, and —PR$^E$—, wherein, $R^E$ independently each occurrence is hydrogen, or a member selected from hydrocarbyl, hydrocarbyloxym, silyl, halogenated alkyl, halogenated aryl, and combinations thereof, said $R^E$ having up to 20 nonhydrogen atoms X is an anionic or dianionic ligand group having up to 60 atoms exclusive of the class of ligands that are cyclic, delocalized, π-bound ligand groups;

X' independently each occurrence is a neutral ligand having up to 40 atoms;

p is zero or 2, and is two less than the formal oxidation state of M when X is an anionic ligand, and when X is a dianionic ligand group, p is 1; and q is zero, 1 or 2.

5. A process according to claim 4 wherein the metal complex is selected from the group consisting of:

dichloro(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium;

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium dimethyl;

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium bis(trimethylsilylmethyl);

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium (dimethylsilylene)bis(methylene);

(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium (II) 1,4-diphenyl-1,3-butadiene;

dichloro(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium;

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium dimethyl;

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium bis(trimethylsilylmethyl);

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium (dimetbylsilylene)bis(methylene);

(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium (II) 1,4-diphenyl-1,3-butadiene;

dichloro(N-(1,1-dimethylethyl)-1,1-di(4-methylphenyl)-1-((1,2,3,3 7a-η)-2-methyl-4-phenyl-1H-inden-1-yl)silanaminato-(2-)-N-)-titanium;

(N-(1,1-dimethylethyl)-1,1-di(4-butylphenyl)-1-((1,2,3,3a,7a-η)-2-methyl-4-phenyl-1H-inden-1-yl)silanaminato-(2-)-N-)-titanium dimethyl;

(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium bis(trimethylsilylmethyl);

(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium (dimethylsilylene)bis(methylene);

(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium (II) 1,4-diphenyl-1,3-butadiene;

dichloro(N-(cyclohexyl)-1,1-di(4-methylphenyl)-1-((1,2,3,3a,7a-η)-2-methyl-4-phenyl-1H-inden-1-yl)silanaminato-(2-)-N-)-titanium;

(N-(cyclohexyl)-1,1-di(4-methylphenyl)-1-((1,2,3,3a,7a-η)-2-methyl-4-phenyl-1H-inden-1-yl)silanaminato-(2-)-N-)-titanium dimethyl;

(N-(cyclohexyl)-1,1-di(4-methylphenyl)-1-((1,2,3,3a,7a-η)-2-methyl-4-phenyl-1H-inden-1-yl)silanaminato-(2-)-N-)-titanium bis(trimethylsilyhnethyl);

(N-(cyclohexyl)-1,1-di(4-methylphenyl)-1-((1,2,3,3a,7a-η)-2-methyl-4-phenyl-1H-1-inden-1-yl)silanaminato-(2-)-N-)-titanium (dimethylsilylene)bis(methylene); and (N-(cyclohexyl)-1,1-di(4-methylphenyl)-1-((1,2,3,3a,7a-η)-2-methyl-4-phenyl-1H-inden-1-yl)silanaminato-(2-)-N-)-titanium (II) 1,4-diphenyl-1,3-butadiene.

6. A process for polymerizing ethylene, optionally at least one diene, and further optionally a $C_{3-12}$ α-olefin by contacting a mixture thereof with a metal complex and an activating cocatalyst under addition polymerization conditions and recovering the resulting polymer product, characterized in that the metal complex is a metal complex corresponding to the formula:

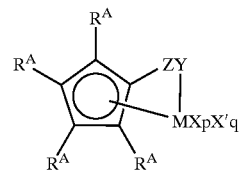

where M is a Group 4 metal that is in the +2, +3 or +4 formal oxidation state;

$R^A$ independently each occurrence is hydrogen, or a hydrocarbyl, halohydrocarbyl, hydrocarbyloxyhydrocarbyl, dihydrocarbylaminohydrocarbyl, dihydrocarbylamino, hydrocarbyloxy, hydrocarbylsilyl, or trihydrocarbylsilylhydrocarbyl group of from 1 to 80 atoms, not counting hydrogen, or optionally, two or more $R^A$ groups may be covalently linked together;

Z is $(R^D)_2Si=$, wherein $R^D$ independently each occurrence is para $C_{1-10}$ alkyl substituted phenyl or two $R^D$ groups together are alkyl- or polyalkyl-substituted arylene of up 40 carbons; and Y is bonded to M and Z and is selected from the group consisting of —O—, —S—, —NR$^E$—, and —PR$^E$—;

wherein, $R^E$ independently each occurrence is hydrogen, or a member selected from hydrocarbyl, hydrocarbyloxy, silyl, halogenated alkyl, halogenated aryl, and combinations thereof, said $R^E$ having up to 20 nonhydrogen atoms X is an anionic or dianionic ligand group having up to 60 atoms exclusive of the class of ligands that are cyclic, delocalized, π-bound ligand groups;

X' independently each occurrence is a neutral ligand having up to 40 atoms;

p is zero or 2, and is two less than the formal oxidation state of M when X is an anionic ligand, and when X is a dianionic ligand group, p is 1; and q is zero, 1 or 2.

7. The process of claim 6 wherein $R^D$ independently each occurrence is para $C_{4-10}$ alkyl substituted phenyl.

8. The process of claim 7 wherein $R^D$ independently each occurrence is 4-(n-butylphenyl).

9. A process according to claim 6 wherein the metal complex is selected from the group consisting of:
dichloro(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium;
(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium dimethyl;
(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium bis(trimethylsilyhnethyl);
(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium (dimethylsilylene)bis(methylene);
(N-(1,1-dimethylethyl)-1,1-di(4-n-butylphenyl)-1-((1,2,3,3a,7a-η)-2-methyl-4-phenyl-1H-inden-1-yl)silanaminato-(2-)-N-)-titanium (II) 1,4-diphenyl-1,3-butadiene;
dichloro(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium;
(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium dimethyl;
(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium bis(trimethylsilylmethyl);
(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium (dimethylsilylene)bis(methylene);
(N-(cyclohexyl)-1,1-di(4-n-butylphenyl)-1-((1,2,3,3a,7a-η)-2-methyl-4-phenyl-1H-inden-1-yl)silanaminato-(2-)-N-)-titanium (II) 1,4-diphenyl-1,3-butadiene;
dichloro(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium;
(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium dimethyl;
(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium bis(trimethylsilylmethyl);
(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium (dimethylsilylene)bis(methylene);
(N-(1,1-dimethylethyl)-1,1-di(4-methylphenyl)-1-((1,2,3,3a,7a-η)-2-methyl-4-phenyl-1H-inden-1-yl)silanaminato-(2-)-N-)-titanium (II) 1,4-diphenyl-1,3-butadiene;
dichloro(N-(cyclohexyl)-1,1-di(4-methylphenyl)-1-((1,2,3,3a,7a-η)-2-methyl-4-phenyl-1H-inden-1-yl)silanaminato-(2-)-N-)-titanium;
(N-(cyclohexyl)-1,1-di(4-methylphenyl)-1-((1,2,3,3a,7a-η)-2-methyl-4-phenyl-1H-inden-1-yl)silanaminato-(2-)-N-)-titanium dimethyl;
(N-(cyclohexyl)-1,1-di(4-methylphenyl)-1-((1,2,3,3a,7a-η)-2-methyl-4-phenyl-1H-inden-1-yl)silanaminato-(2-)-N-)-titanium bis(trimethylsilylmethyl);
(N-(cyclohexyl)-1,1-di(4-methylphenyl)-1-((1,2,3,3a,7a-η)-2-methyl-4-phenyl-1H-inden-1-yl)silanaminato-(2-)-N-)-titanium (dimethylsilylene)bis(methylene); and
(N-(cyclohexyl)-1,1-di(4-methylphenyl)-1-((1,2,3,3a,7a-η)-2-methyl-4-phenyl-1H-inden-1-yl)silanaminato-(2-)-N-)-titanium (II) 1,4-diphenyl-1,3-butadiene.

10. The process according to claim 6 wherein two $R^D$ groups together are alkyl- or polyalkyl- substituted arylene of up to 40 carbons.

11. A process for polymerizing ethylene, optionally at least one diene, and further optionally a $C_{3-12}$ α-olefin by contacting a mixture thereof with a metal complex and an activating cocatalyst under addition polymerization conditions and recovering the resulting polymer product, characterized in that the metal complex is a metal complex corresponding to the formula:

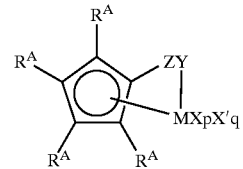

where M is a Group 4 metal that is in the +2, +3 or +4 formal oxidation state;

$R^A$ independently each occurrence is hydrogen, or a hydrocarbyl, halohydrocarbyl, hydrocarbyloxyhydrocarbyl, dihydrocarbylaminohydrocarbyl, dihydrocarbylamino, hydrocarbyloxy, hydrocarbylsilyl, or trihydrocarbylsilylhydrocarbyl group of from 1 to 80 atoms, not counting hydrogen, or optionally, two or more $R^A$ groups may be covalently linked together;

Z is $(R^D)_2Si=$, wherein $R^D$ independently each occurrence is $C_{4-10}$ alkyl substituted phenyl; and Y is bonded to M and Z and is selected from the group consisting of —O—, —S—, —$NR^E$—, and —$PR^E$—; wherein, $R^E$ independently each occurrence is hydrogen, or a member selected from hydrocarbyl, hydrocarbyloxy, silyl, halogenated alkyl, halogenated aryl, and combinations thereof, said $R^E$ having up to 20 nonhydrogen atoms X is an anionic or dianionic ligand group having up to 60 atoms exclusive of the class of ligands that are cyclic, delocalized, π-bound ligand groups;

X' independently each occurrence is a neutral ligand having up to 40 atoms;

p is zero or 2, and is two less than the formal oxidation state of M when X is an anionic ligand, and when X is a dianionic ligand group, p is 1; and q is zero, 1 or 2.

12. A process for polymerizing ethylene, at least one diene, and optionally a $C_{3-12}$ α-olefin by contacting a mixture thereof with a metal complex and an activating cocatalyst under addition polymerization conditions and recovering the resulting polymer product, characterized in that the metal complex is a metal complex corresponding to the formula:

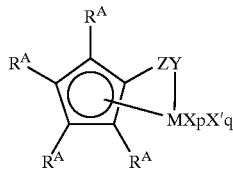

where M is a Group 4 metal that is in the +2, +3 or +4 formal oxidation state;

$R^A$ independently each occurrence is hydrogen, or a hydrocarbyl, halohydrocarbyl, hydrocarbyloxyhydrocarbyl, dihydrocarbylaminohydrocarbyl, dihydrocarbylamino, hydrocarbyloxy, hydrocarbylsilyl, or trihydrocarbylsilylhydrocarbyl group of from 1 to 80 atoms, not counting hydrogen, or optionally, two or more $R^A$ groups may be covalently linked together;

Z is $(R^D)_2Si=$, wherein $R^D$ independently each occurrence is $C_{4-10}$ alkyl substituted phenyl; and Y is bonded to M and Z and is selected from the group consisting of —O—, —S—, —$NR^E$—, and —$PR^E$—; wherein, $R^E$ independently each occurrence is hydrogen, or a member selected from hydrocarbyl, hydrocarbyloxy, silyl, halogenated alkyl, halogenated aryl, and combinations thereof, said $R^E$ having up to 20 nonhydrogen atoms X is an anionic or dianionic ligand group having up to 60 atoms exclusive of the class of ligands that are cyclic, delocalized, π-bound ligand groups;

X' independently each occurrence is a neutral ligand having up to 40 atoms;

p is zero or 2, and is two less than the formal oxidation state of M when X is an anionic ligand, and when X is a dianionic ligand group, p is 1; and q is zero, 1 or 2.

13. A process for polymerizing ethylene, optionally at least one diene, and further optionally a $C_{3-12}$ α-olefin by contacting a mixture thereof with a metal complex and an activating cocatalyst under addition polymerization conditions and recovering the resulting polymer product, characterized in that the metal complex is a metal complex corresponding to the formula:

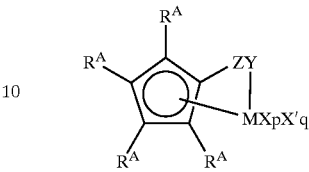

where M is a Group 4 metal that is in the +2, +3 or +4 formal oxidation state;

$R^A$ independently each occurrence is hydrogen, or a hydrocarbyl, halohydrocarbyl, hydrocarbyloxyhydrocarbyl, dihydrocarbylaminohydrocarbyl, dihydrocarbylamino, hydrocarbyloxy, hydrocarbylsilyl, or trihydrocarbylsilylhydrocarbyl group of from 1 to 80 atoms, not counting hydrogen, or optionally, two or more $R^A$ groups may be covalently linked together;

Z is $(R^D)_2Si=$, wherein two $R^D$ groups together are alkyl- or polyalkyl-subsituted arylene of up to 40 carbons; and Y is bonded to M and Z and is selected from the group consisting of —O—, —S—, $NR^E$—, and —$PR^E$—; wherein, $R^E$ independently each occurrence is hydrogen, or a member selected from hydrocarbyl, hydrocarbyloxy, silyl, halogenated alkyl, halogenated aryl, and combinations thereof, said $R^E$ having up to 20 nonhydrogen atoms X is an anionic or dianionic ligand group having up to 60 atoms exclusive of the class of ligands that are cyclic, delocalized, π-bound ligand groups;

X' independently each occurrence is a neutral ligand having up to 40 atoms;

p is zero or 2, and is two less than the formal oxidation state of M when X is an anionic ligand, and when X is a dianionic ligand group, p is 1; and q is zero, 1 or 2.

* * * * *